United States Patent [19]
Smith et al.

[11] Patent Number: 5,559,021
[45] Date of Patent: Sep. 24, 1996

[54] DNA ENCODING A NOVEL MAMMALIAN TRANSPORTER HOMOLOGOUS TO NEUROTRANSMITTER TRANSPORTERS AND USES THEREOF

[75] Inventors: Kelli E. Smith, Wayne, N.J.; Richard L. Weinshank, New York, N.Y.

[73] Assignee: Synaptic Pharmaceutical Corporation, Paramus, N.J.

[21] Appl. No.: 149,100

[22] Filed: Nov. 9, 1993

[51] Int. Cl.⁶ .............................. C12N 5/06; C12N 1/21; C12N 1/19; C12N 15/63
[52] U.S. Cl. ............................ 435/240.2; 435/252.3; 435/254.2; 435/320.1; 536/23.5
[58] Field of Search ................... 435/252.30, 320.1, 435/240.2, 254.2; 536/23.5, 24.31; 935/69, 70, 71, 72

[56] References Cited

FOREIGN PATENT DOCUMENTS 9318143   9/1993   WIPO .

OTHER PUBLICATIONS

Smith, K. E. et al. (1993) "Cloning of a rat brain cDNA encoding a novel 'orphan' transporter" *Soc. Neurosci: Abstr.* 19(1):747.

*Primary Examiner*—Charles L. Patterson, Jr.
*Assistant Examiner*—Kawai Lau
*Attorney, Agent, or Firm*—John P. White

[57] ABSTRACT

This invention provides an isolated nucleic acid molecule encoding a mammalian rB21a transporter, an isolated protein which is a mammalian rB21a transporter, vectors comprising an isolated nucleic acid molecule encoding a mammalian rB21a transporter, mammalian cells comprising such vectors, antibodies directed to the mammalian rB21a transporter, nucleic acid probes useful for detecting a nucleic acid molecule encoding mammalian rB21a transporter, antisense oligonucleotides complementary to any unique sequences of a nucleic acid molecule which encodes a mammalian rB21a transporter, pharmaceutical compounds related to mammalian rB21a transporter, and nonhuman transgenic animals which express DNA encoding a normal or a mutant mammalian rB21a transporter. This invention further provides methods for determining substrate binding, detecting expression, drug screening, and treatments for alleviating abnormalities associated with the mammalian rB21a transporter.

15 Claims, 13 Drawing Sheets

FIGURE 1A

```
         -270                    -250                 -230
           .                       .                    .
GTTAACAATAACTGATCCCGTGGTATTTAAACGTTCCCGCCATCTGAATGTAAGCCCTGG

-210                    -190                 -170
           .                       .                    .
AAGAGTGGGGGTGCTATGTTTTCCTGTTGCACAGCAGTGCCAGGCAGATAGTATTGTCCT

-150                    -130                 -110
           .                       .                    .
CGATTAATCAGTAAGAAGTTGAGGAAACGTGATCCTTTCCCCGAGCTCTGAAGTCCACAC

-90                     -70                  -50
           .                       .                    .
CCCGGACCAAGGAGGGGCGCCTTCCCCGCCGAGGCTAGGCAGGGTGGGGCTCACCGCTCC

-30                     -10                   10
           .                       .                    .
CCACTTACCGGCCTCGCCCCTCTCGTGCGCGTTAATGAGATTAGCAATTAAAAGGCGGGC
                                        M   R   L   A   I   K   R   R   A 30                      50                   70
            .                       .                    .
GAGCCGCGGCCAGAGACCAGGCCCTGACGAGAAGCGAGCGCGGGACATGGAGAAGGCACG
 S   R   G   Q   R   P   G   P   D   E   K   R   A   R   D   M   E   K   A   R 90                     110                  130
            .                       .                    .
GCCTCAATGGGGCAATCCGCTGCAGTTCGTTTTCGCCTGTATCTCCTACGCCGTGGGTTT
 P   Q   W   G   N   P   L   Q   F   V   F   A   C   I   S   Y   A   V   G   L 150                     170                  190
            .                       .                    .
GGGCAATGTGTGGCGCTTCCCCTACCTGTGCCAGATGTACGGCGGAGGGAGTTTCCTGGT
 G   N   V   W   R   F   P   Y   L   C   Q   M   Y   G   G   S   F   L   V 210                     230                  250
            .                       .                    .
CCCCTACCTCATCATGCTCATTGTGGAGGGGATGCCACTCTTGTACCTGGAGCTGGCTGT
 P   Y   L   I   M   L   I   V   E   G   M   P   L   L   Y   L   E   L   A   V 270                     290                  310
            .                       .                    .
GGGGCAGCGCATGCGGCAGGGCAGCATTGGTGCCTGGAGGACCATCAGCCCCTACCTTAG
 G   Q   R   M   R   Q   G   S   I   G   A   W   R   T   I   S   P   Y   L   S
```

FIGURE 1B

```
        330                 350                 370
         .                   .                   .
TGGTGTCGGTGTTGCCAGTGTGGTGGTCTCCTTCTTCCTCTCCATGTACTACAATGTCAT
 G  V  G  V  A  S  V  V  V  S  F  F  L  S  M  Y  Y  N  V  I 390                 410                 430
         .                   .                   .
CAATGCCTGGGGCTTCTGGTACCTCTTCCACTCCTTCCAGGATCCCCTGCCGTGGTCTGT
 N  A  W  G  F  W  Y  L  F  H  S  F  Q  D  P  L  P  W  S  V 450                 470                 490
         .                   .                   .
CTGCCCACTGAATAGTAACCGCACAGGCTATGATGAGGAGTGTGAGAAGGCTTCGTCGAC
 C  P  L  N  S  N  R  T  G  Y  D  E  E  C  E  K  A  S  S  T 510                 530                 550
         .                   .                   .
ACAGTACTTCTGGTACAGGAAAACACTCAACATCTCACCGTCCATCCAGGAGAATGGAGG
 Q  Y  F  W  Y  R  K  T  L  N  I  S  P  S  I  Q  E  N  G  G 570                 590                 610
         .                   .                   .
AGTGCAGTGGGAGCCAGCCCTGTGCCTCACCCTGGCCTGGCTGATGGTATATCTGTGCAT
 V  Q  W  E  P  A  L  C  L  T  L  A  W  L  M  V  Y  L  C  I 630                 650                 670
         .                   .                   .
CCTGAGAGGCACCGAATCTACTGGCAAGGTGGTCTACTTCACCGCATTGATGCCTTACTG
 L  R  G  T  E  S  T  G  K  V  V  Y  F  T  A  L  M  P  Y  C 690                 710                 730
         .                   .                   .
TGTTCTTATTATCTACTTGGTCCGTGGCCTCACACTCCATGGAGCCACCAATGGCCTGAT
 V  L  I  I  Y  L  V  R  G  L  T  L  H  G  A  T  N  G  L  M 750                 770                 790
         .                   .                   .
GTACATGTTCACACCTAAGATTGAGCAGCTAGCCAACCCCAAGGCCTGGATCAATGCAGC
 Y  M  F  T  P  K  I  E  Q  L  A  N  P  K  A  W  I  N  A  A 810                 830                 850
         .                   .                   .
CACGCAGATCTTCTTCTCACTGGGCTTGGGTTTTGGCAGCCTGATCGCTTTTGCCAGCTA
 T  Q  I  F  F  S  L  G  L  G  F  G  S  L  I  A  F  A  S  Y 870                 890                 910
         .                   .                   .
CAATGAACCCTCCAACGACTGCCAGAAGCATGCTGTCATTGTGTCTGTCATCAACAGCTC
 N  E  P  S  N  D  C  Q  K  H  A  V  I  V  S  V  I  N  S  S
```

FIGURE 1C

```
      930                 950                 970
       .                   .                   .
CACCTCCATATTTGCCAGCATTGTCACCTTCTCCATCTATGGCTTCAAGGCCACCTTCAA
 T  S  I  F  A  S  I  V  T  F  S  I  Y  G  F  K  A  T  F  N 990                1010                1030
       .                   .                   .
CTATGAAAACTGCTTAAACAAGGTGATTCTGCTGCTGACCAATTCTTTTGACCTTGAAGA
 Y  E  N  C  L  N  K  V  I  L  L  L  T  N  S  F  D  L  E  D 1050                1070                1090
       .                   .                   .
TGGCTTTCTGACAGCCAGCAACCTGGAGGAGGTGAAGGACTACCTGGCATCTACTTACCC
 G  F  L  T  A  S  N  L  E  E  V  K  D  Y  L  A  S  T  Y  P 1110                1130                1150
       .                   .                   .
AAACAAGTACAGTGAAGTGTTCCCACACATTAGAAACTGCAGCTTGGAATCAGAGCTGAA
 N  K  Y  S  E  V  F  P  H  I  R  N  C  S  L  E  S  E  L  N 1170                1190                1210
       .                   .                   .
CACGGCTGTCCAAGGCACAGGCCTGGCCTTCATCGTCTACGCTGAGGCCATTAAAAACAT
 T  A  V  Q  G  T  G  L  A  F  I  V  Y  A  E  A  I  K  N  M 1230                1250                1270
       .                   .                   .
GGAAGTGTCCCAGCTCTGGTCAGTGCTCTACTTCTTCATGCTGCTGATGCTGGGAATGGG
 E  V  S  Q  L  W  S  V  L  Y  F  F  M  L  L  M  L  G  M  G 1290                1310                1330
       .                   .                   .
GAGCATGCTTGGAAATACAGCGGCCATCCTCACCCCTCTGACTGACAGCAAGGTCATCTC
 S  M  L  G  N  T  A  A  I  L  T  P  L  T  D  S  K  V  I  S 1350                1370                1390
       .                   .                   .
CAGCTACCTGCCCAAGGAGGCCATTTCAGGTCTGGTGTGCCTCATTAACTGTGCTGTTGG
 S  Y  L  P  K  E  A  I  S  G  L  V  C  L  I  N  C  A  V  G 1410                1430                1450
       .                   .                   .
CATGGTGTTCACCATGGAGGCTGGGAACTACTGGTTTGACATATTCAATGACTATGCAGC
 M  V  F  T  M  E  A  G  N  Y  W  F  D  I  F  N  D  Y  A  A 1470                1490                1510
       .                   .                   .
CACGCTGTCTCTGCTGCTCATTGTGCTGGTGGAGACTATAGCTGTGTGCTACGTGTATGG
 T  L  S  L  L  L  I  V  L  V  E  T  I  A  V  C  Y  V  Y  G
```

FIGURE 1D

```
1530                  1550                  1570
  .                     .                     .
GCTGAGGAGATTTGAAAGTGATCTTCGGGCCATGACTGGCCGGCCCCTCAACTGGTACTG
 L  R  R  F  E  S  D  L  R  A  M  T  G  R  P  L  N  W  Y  W 1590                  1610                  1630
  .                     .                     .
GAAGGCCATGTGGGCTTTTGTGAGCCCACTGCTCATCATCGGCCTCTTTATCTTCTACCT
 K  A  M  W  A  F  V  S  P  L  L  I  I  G  L  F  I  F  Y  L 1650                  1670                  1690
  .                     .                     .
GAGTGACTACATCCTCACGGGAACGCTGCAGTACCAAGCCTGGGATGCTACTCAGGGGCA
 S  D  Y  I  L  T  G  T  L  Q  Y  Q  A  W  D  A  T  Q  G  Q 1710                  1730                  1750
  .                     .                     .
GCTGGTGACCAAGGATTACCCTCCACATGCACTAGCTGTCATCGGTTTGCTGGTGGCTTC
 L  V  T  K  D  Y  P  P  H  A  L  A  V  I  G  L  L  V  A  S 1770                  1790                  1810
  .                     .                     .
ATCTACTATGTGCATCCCCCTGGTGGCCCTGGGGACTTTCATCAGGAATCGCCTCAAGAG
 S  T  M  C  I  P  L  V  A  L  G  T  F  I  R  N  R  L  K  R 1830                  1850                  1870
  .                     .                     .
GGGAGGCTCTTCCCCAGTGGCCTAAGAATGGACCTCCCAAAGACCGAAGTCAGCCACTCT
 G  G  S  S  P  V  A  *

1890                  1910                  1930
  .                     .                     .
GTTTCACAGTTACCACCTGCTGGTGGGATCTTCTTGGCTGGAGTGCTGGTCTGTGGCCTC 1950                  1970                  1990
  .                     .                     .
CTGAGTCTGTATAGAAGATGAGAGAGCTTAGCAAAAGAAGACTGCCTTGGGGAGGGGACC 2010                  2030                  2050
  .                     .                     .
ACATCCCTTAGGAGGGGCCCTCCATCCTCTGCCGTCTGAAGGTCATACCTTATAGCCTCT 2070                  2090                  2110
  .                     .                     .
TTGTCATCAAAGGTTAAGGCCAGTATTGAAGATTGTTGTTTTCTTGATTCTAGAAAGTTC 2130                  2150                  2170
  .                     .                     .
TAGAATTTAAGGTAAACTGTCATTAGAAACTTGACTGTAACTCTAAGGAGCCAAACAAGC
```

FIGURE 1E

```
2190                    2210                    2230
AATTACATTTTTTTTATTGTTGTTGTTGTTGTTTAAAAGAAAACAAAATACTAGAGGGTA 2250                    2270                    2290
TTTGCTTTTCAACCAGTGTCAGAGGTTTTGAAGCATGAAAGGTGACAAATTAAATTTAAT 2310                    2330                    2350
CTAGCTCTTTTCTATAAAGTCACAATGAATGTGCAATTTCTCTGTTCCCTGACTACTCTC 2370                    2390                    2410
TATATGTTACCAGGATATAATAGCCACTAAGAGACTTTTTCTGGGGTTCCAATGGACGTC 2430                    2450                    2470
ACCTTTCTCTGAATCTAAGGTTCCTCACAGTGGGCCAGGACCAACCTCTCTACAACTCTA 2490                    2510                    2530
GACTGCACAAGGAATCTGAACAGACACTCCCATCTCTAGGGTTTCAGTGTCAGATGCATC 2550                    2570                    2590
TATAAGGATACAAGTAACTCTAACTTTGCTATAAATATCACTCGCGACCACCTTCATTCA 2610                    2630                    2650
CTTCTGAATAATAATGTTTTCTAAAATGTATATAAATCACACAGAGCAGTGTGTAGCTGA 2670                    2690                    2710
AAATACTCCATATTTATGGCTGTTATCCATGCACCATGTGAATATGTCTCTTTTTTATCG 2730                    2750
TAATAAAGTGAATCAAGGTTATCT
```

FIGURE 2A

```
              1                                                              50
    rB21a     ..........  ..........  ..........  .....MRLAI  KRRASRGQRP
     Gat2     ..........  ..........  ..........  ..MDNRVSGT  TSNGETKPVC
  Taurine     ..........  ..........  ...MATKEKL  QCLKDFHKDI  LKPSPGKSPG
   Norepi     ........ML  LARMNPQVQP  ENNGADTGPE  QPLRARKTAE  LLVVKERNGV
  Glycine     ..........  ..........  ..MAVAHGPV  ATSSPEQNGA 51                              I                         100
    rB21a     GPDEKRARDM  EKARPQWGNP  LQFVFACISY  AVGLGNVWRF  PYLCQMYGGG
     Gat2     PVMEKVEEDG  TLEREQWTNK  MEFVLSVAGE  IIGLGNVWRF  PYLCYKNGGG
  Taurine     TRPEDEADGK  PPQREKWSSK  IDFVLSVAGG  FVGLGNVWRF  PYLCYKNGGG
   Norepi     QCLLAPRDGD  AQPRETWGKK  IDFLLSVVGF  AVDLANVWRF  PYLCYKNGGG
  Glycine     VPSEATKKDQ  NLTRGNWGNQ  IEFVLTSVGY  AVGLGNVWRF  PYLCYRNGGG 101    II                                                  150
    rB21a     SFLVPYLIML  IVEGMPLLYL  ELAVGQRMRQ  GSIGAWRTIS  PYLSGVGVAS
     Gat2     AFFIPYLIFL  FTCGIPVFFL  ETALGQYTNQ  GGITAWRKIC  PIFEGIGYAS
  Taurine     AFLIPYFIFL  FGSGLPVFFL  EVIIGQYTSE  GGITCWEKIC  PLFSGIGYAS
   Norepi     AFLIPYTLFL  IIAGMPLFYM  ELALGQYNRE  GAATVW.KIC  PFFKGVGYAV
  Glycine     AFMFPYFIML  VFCGIPLFFM  ELSFGQFASQ  GCLGVW.RIS  PMFKGVGYGM 151    III                                                 200
    rB21a     VVVSFFLSMY  YNVINAWGFW  YLFHSFQDPL  PWSVCPLNSN  RT..GYDEEC
     Gat2     QMIVSLLNVY  YIVVLAWALF  YLFSSFTTDL  PWGSCSHEWN  TENCVE...F
  Taurine     IVIVSLLNVY  YIVILAWATY  YLFQSFQKDL  PWAHCNHSWN  TPQCMEDTLR
   Norepi     ILIALYVGFY  YNVIIAWSLY  YLFSSFTLNL  PWTDCGHTWN  SPNCTDPKLL
  Glycine     MVVSTYIGIY  YNVVICIAFY  YFFSSMTHVL  PWAYCNNPWN  TPDCAGVLDA 201                                                        250
    rB21a     EK........  ..........  ......ASST  QYFWYRKTLN  I..SPSIQEN
     Gat2     QKT..NNSLN  VTSENA....  ......TSPV  IEFWERRVLK  I..SDGIQHL
  Taurine     RNE..SHWVS  LSAANF....  ......TSPV  IEFWERNVLS  L..SSGIDHP
   Norepi     NGSVLGNHTK  YSKYKF....  ......T.PA  AEFYERGVLH  LHESSGIHDI
  Glycine     SNLTNGSRPT  ALSGNLSHLF  NYTLQRTSPS  EEYWRLYVLK  L..SDDIGDF 251         IV                          V                  300
    rB21a     GGVQWEPALC  LTLAWLMVYL  CILRGTESTG  KVVYFTALMP  YCVLIIYLVR
     Gat2     GSLRWELVLC  LLLAWIICYF  CIWKGVKSTG  KVVYFTATFP  YLMLVVLLIR
  Taurine     GSLKWDLALC  LLLVWLVCFF  CIWKGVRSTG  KVVYFTATFP  FAMLLVLLVR
   Norepi     GLPQWQLLLC  LMVVVIVLYF  SLWKGVKTSG  KVVWITATLP  YFVLFVLLVH
  Glycine     GEVRLPLLGC  LGVSWVVVFL  CLIRGVKSSG  KVVYFTATFP  YVVLTILFVR 301                                            VI          350
    rb21a     GLTLHGATNG  LMYMFTPKIE  QLANPKAWIN  AATQIFFSLG  LGFGSLIAFA
     Gat2     GVTLPGAAQG  IQFYLYPNIT  RLWDPQVWMD  AGTQIFFSFA  ICLGCLTALG
  Taurine     GLTLPGAGEG  IKFYLYPNIS  RLEDPQVWID  AGTQIFFSYA  ICLGAMTSLG
   Norepi     GVTLPGASNG  INAYLHIDFY  RLKEATVWID  AATQIFFSLG  AGFGVLIAFA
  Glycine     GVTLEGAFTG  IMYYLTPKWD  KILEAKVWGD  AASQIFYSLG  CAWGGLITMA
```

FIGURE 2B

```
              351                        VII                           400
    rB21a  SYNEPSNDCQ KHAVIVSVIN SSTSIFASIV TFSIYGFKAT FNYENCL...
     Gat2  SYNKYHNNCY RDCVALCILN SSTSFVAGFA IFSILGFMSQ EQ........
  Taurine  SYNKYKYNSY RDCMLLGCLN SGTSFVSGFA IFSILGFMAQ EQ........
   Norepi  SYNKFDNNCY RDALLTSSIN CITSFVSGFA IFSILGYMAH EH........
  Glycine  SYNKFHNNCY RDSVIISITN CATSVYAGFV IFSILGFMAN HL........

401                                                       450
    rB21a  NKVILLLTNS FDLEDGF...  ......LTAS NLEEVKDYLA STYPNKYSEV
     Gat2  .......... ..........  ........GV PISEV..... ..........
  Taurine  .......... ..........  ........GV DIADV..... ..........
   Norepi  .......... ..........  ........KV NIEDV..... ..........
  Glycine  .......... ..........  ........GV DVSRV..... ..........

451                                  VIII              500
    rB21a  FPHIRNCSLE SELNTAVQGT GLAFIVYAEA IKNMEVSQLW SVLYFFMLLM
     Gat2  .......... .....AESGP GLAFIAYPRA VVMLPFSPLW ACCFFFMVVL
  Taurine  .......... .....AESGP GLAFIAYPKA VTMMPLPTFW SILFFIMLLL
   Norepi  .......... .....ATEGA GLVFILYPEA ISTLSGSTFW AVVFFVMLLA
  Glycine  .......... .....ADHGP GLAFVAYPEA LTLLPISPLW SLLFFFMLIL 501                                    IX               550
    rB21a  LGMGSMLGNT AAILTPLTDS K..VISSYLP KEAISGLVCL INCAVGMVFT
     Gat2  LGLDSQFVCV ESLVTALVDM YPRVFRKKNR REILILIVSV VSFFIGLIML
  Taurine  LGLDSQFVEV EGQITSLVDL YPSFLRKGYR REIFIAIVCS ISYLLGLTMV
   Norepi  LGLDSSMGGM EAVITGLADD FQVLKR...H RKLFTFGVTF STFLLALFCI
  Glycine  LGLGTQFCLL ETLVTAIVDE VGN.EWILQK KTYVTLGVAV AGFLLGIPLT 551                        X                            600
    rB21a  MEAGNYWFDI FNDYAA.TLS LLLIVLVETI AVCYVYGLRR FESDLRAMTG
     Gat2  TEGGMYVFQL FDYYAASGMC LLFVAIFESL CVAWVYGASR FYDNIEDMIG
  Taurine  TEGGMYVFQL FDYYAASGVC LLWVAFFECF VIAWIYGGDN LYDGIEDMIG
   Norepi  TKGGIYVLTL LDTFAA.GTS ILFAVLMEAI GVSWFYGVDR FSNDIQQMMG
  Glycine  SQAGIYWLLL MDNYAAS.FS LVVISCIMCV SIMYIYGHRN YFQDIQMMLG 601         XI                                          650
    rB21a  RPLNWYWKAM WAFVSPLLII GLFIFYLSDY ILTGTLQYQA WDATQGQLVT
     Gat2  YKPWPLIKYC WLFFTPAVCL ATFLFSLIKY ...TPLTYN. ........KK
  Taurine  YRPGPWMKYS WAVITPALCV GCFIFSLVKY ...VPLTYN. ........KV
   Norepi  FRPGLYWRLC WKFVSPAFLL FVVVVSIINF ...KPLTYD. ........D.
  Glycine  FPPPLFFQIC WRFVSPTIIF FILIFTVIQY ...RPITYN. ........H.

651         XII                                         700
    rB21a  KDYPPHALAV IGLLVASSTM CIPLVALGTF IRNRLKRGGS SPVA......
     Gat2  YTYPWWGDAL GWLLALSSMV CIPAWSI... ..YKLRTKG .PLRERLRQL
  Taurine  YRYPDWAIGL GWGLALSSMV CIPLVIV... ..ILLCRTEG .PLRVRIKYL
   Norepi  YIFPPWANWV GWGIALSSMV LVPIYVI... ..YKFLSTQG .SLWERLAYG
  Glycine  YQYPGWAVAI GFLMALSSVI CIPLYAL... ..FQLCRTDG DTLLQRLKNA
```

FIGURE 2C

```
            701                                                           750
   rB21a    ..........  ..........  ..........  ..........  ..........
    Gat2    VCPAE....D  LPQKSQPELT  SPATPM.TSL  LRLTELESNC  ..........
 Taurine    ITPREPNRWA  VEREGATPFH  SRATLMNGAL  MKPSHVIVET  MM........
  Norepi    ITP.ENEHHL  VAQRDIRQFQ  LQHWLAI...  ..........  ..........
 Glycine    TKPSRDWGPA  LLEHRTGRYA  PTTTPSPEDG  FEVQPLHPDK  AQIPIVGSNG 751
   Rb21a    ..........
    Gat2    ..........
 Taurine    ..........
  Norepi    ..........
 Glycine    SSRLQDSRI.
```

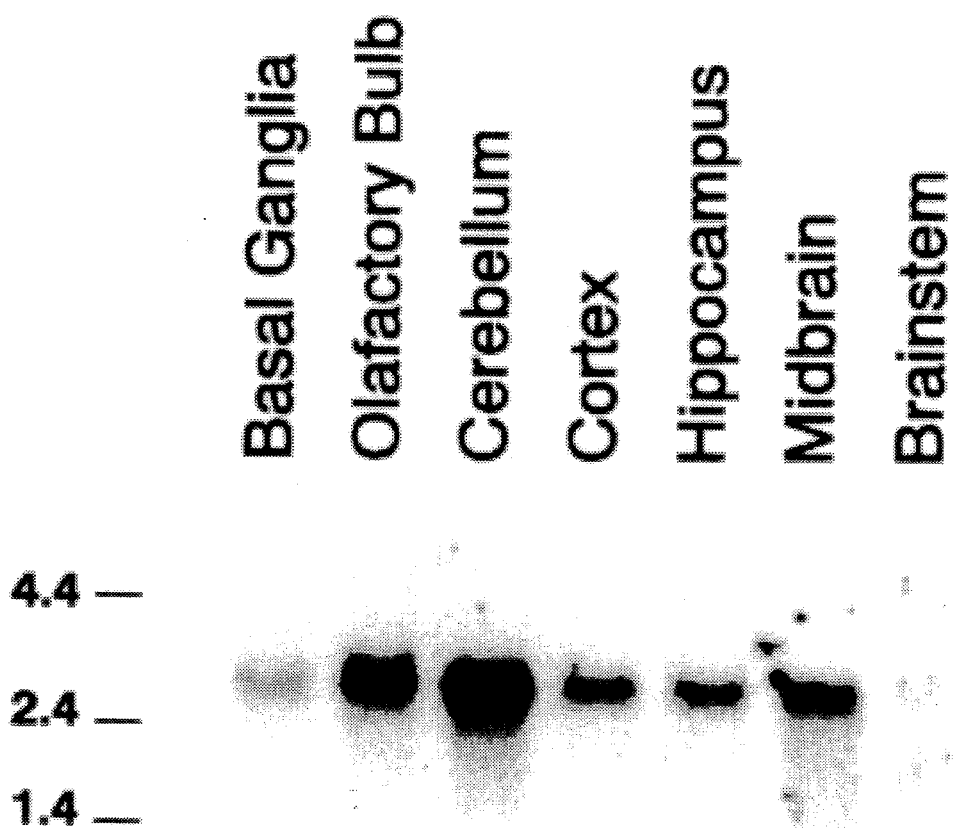

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 3024 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 275..2122

( x i ) SEQUENCE DESCRIPTION: SEQ ID NO:1:

```
GTTAACAATA ACTGATCCCG TGGTATTTAA ACGTTCCCGC CATCTGAATG TAAGCCCTGG        60

AAGAGTGGGG GTGCTATGTT TTCCTGTTGC ACAGCAGTGC CAGGCAGATA GTATTGTCCT       120

CGATTAATCA GTAAGAAGTT GAGGAAACGT GATCCTTTCC CCGAGCTCTG AAGTCCACAC       180

CCCGGACCAA GGAGGGCGC  CTTCCCCGCC GAGGCTAGGC AGGGTGGGGC TCACCGCTCC       240

CCACTTACCG GCCTCGCCCC TCTCGTGCGC GTTA ATG AGA TTA GCA ATT AAA           292
                                     Met Arg Leu Ala Ile Lys
                                       1                 5

AGG CGG GCG AGC CGC GGC CAG AGA CCA GGC CCT GAC GAG AAG CGA GCG         340
Arg Arg Ala Ser Arg Gly Gln Arg Pro Gly Pro Asp Glu Lys Arg Ala
            10                  15                  20

CGG GAC ATG GAG AAG GCA CGG CCT CAA TGG GGC AAT CCG CTG CAG TTC         388
Arg Asp Met Glu Lys Ala Arg Pro Gln Trp Gly Asn Pro Leu Gln Phe
        25                  30                  35

GTT TTC GCC TGT ATC TCC TAC GCC GTG GGT TTG GGC AAT GTG TGG CGC         436
Val Phe Ala Cys Ile Ser Tyr Ala Val Gly Leu Gly Asn Val Trp Arg
    40                  45                  50

TTC CCC TAC CTG TGC CAG ATG TAC GGC GGA GGG AGT TTC CTG GTC CCC         484
Phe Pro Tyr Leu Cys Gln Met Tyr Gly Gly Gly Ser Phe Leu Val Pro
55              60                  65                  70

TAC CTC ATC ATG CTC ATT GTG GAG GGG ATG CCA CTC TTG TAC CTG GAG         532
Tyr Leu Ile Met Leu Ile Val Glu Gly Met Pro Leu Leu Tyr Leu Glu
                75                  80                  85

CTG GCT GTG GGG CAG CGC ATG CGG CAG GGC AGC ATT GGT GCC TGG AGG         580
Leu Ala Val Gly Gln Arg Met Arg Gln Gly Ser Ile Gly Ala Trp Arg
            90                  95                 100

ACC ATC AGC CCC TAC CTT AGT GGT GTC GGT GTT GCC AGT GTG GTG GTC         628
Thr Ile Ser Pro Tyr Leu Ser Gly Val Gly Val Ala Ser Val Val Val
           105                 110                 115

TCC TTC TTC CTC TCC ATG TAC TAC AAT GTC ATC AAT GCC TGG GGC TTC         676
Ser Phe Phe Leu Ser Met Tyr Tyr Asn Val Ile Asn Ala Trp Gly Phe
       120                 125                 130

TGG TAC CTC TTC CAC TCC TTC CAG GAT CCC CTG CCG TGG TCT GTC TGC         724
Trp Tyr Leu Phe His Ser Phe Gln Asp Pro Leu Pro Trp Ser Val Cys
135                 140                 145                 150

CCA CTG AAT AGT AAC CGC ACA GGC TAT GAT GAG GAG TGT GAG AAG GCT         772
Pro Leu Asn Ser Asn Arg Thr Gly Tyr Asp Glu Glu Cys Glu Lys Ala
                155                 160                 165
```

| | | | | | | | | | | | | | | | | |
|---|---|---|---|---|---|---|---|---|---|---|---|---|---|---|---|---|
| TCG | TCG | ACA | CAG | TAC | TTC | TGG | TAC | AGG | AAA | ACA | CTC | AAC | ATC | TCA | CCG | 820 |
| Ser | Ser | Thr | Gln | Tyr | Phe | Trp | Tyr | Arg | Lys | Thr | Leu | Asn | Ile | Ser | Pro | |
| | | | 170 | | | | | 175 | | | | | 180 | | | |
| TCC | ATC | CAG | GAG | AAT | GGA | GGA | GTG | CAG | TGG | GAG | CCA | GCC | CTG | TGC | CTC | 868 |
| Ser | Ile | Gln | Glu | Asn | Gly | Gly | Val | Gln | Trp | Glu | Pro | Ala | Leu | Cys | Leu | |
| | | 185 | | | | | 190 | | | | | 195 | | | | |
| ACC | CTG | GCC | TGG | CTG | ATG | GTA | TAT | CTG | TGC | ATC | CTG | AGA | GGC | ACC | GAA | 916 |
| Thr | Leu | Ala | Trp | Leu | Met | Val | Tyr | Leu | Cys | Ile | Leu | Arg | Gly | Thr | Glu | |
| | 200 | | | | | 205 | | | | | 210 | | | | | |
| TCT | ACT | GGC | AAG | GTG | GTC | TAC | TTC | ACC | GCA | TTG | ATG | CCT | TAC | TGT | GTT | 964 |
| Ser | Thr | Gly | Lys | Val | Val | Tyr | Phe | Thr | Ala | Leu | Met | Pro | Tyr | Cys | Val | |
| 215 | | | | 220 | | | | | 225 | | | | | 230 | | |
| CTT | ATT | ATC | TAC | TTG | GTC | CGT | GGC | CTC | ACA | CTC | CAT | GGA | GCC | ACC | AAT | 1012 |
| Leu | Ile | Ile | Tyr | Leu | Val | Arg | Gly | Leu | Thr | Leu | His | Gly | Ala | Thr | Asn | |
| | | | | 235 | | | | | 240 | | | | | 245 | | |
| GGC | CTG | ATG | TAC | ATG | TTC | ACA | CCT | AAG | ATT | GAG | CAG | CTA | GCC | AAC | CCC | 1060 |
| Gly | Leu | Met | Tyr | Met | Phe | Thr | Pro | Lys | Ile | Glu | Gln | Leu | Ala | Asn | Pro | |
| | | | 250 | | | | | 255 | | | | | 260 | | | |
| AAG | GCC | TGG | ATC | AAT | GCA | GCC | ACG | CAG | ATC | TTC | TTC | TCA | CTG | GGC | TTG | 1108 |
| Lys | Ala | Trp | Ile | Asn | Ala | Ala | Thr | Gln | Ile | Phe | Phe | Ser | Leu | Gly | Leu | |
| | | 265 | | | | | 270 | | | | | 275 | | | | |
| GGT | TTT | GGC | AGC | CTG | ATC | GCT | TTT | GCC | AGC | TAC | AAT | GAA | CCC | TCC | AAC | 1156 |
| Gly | Phe | Gly | Ser | Leu | Ile | Ala | Phe | Ala | Ser | Tyr | Asn | Glu | Pro | Ser | Asn | |
| | 280 | | | | | 285 | | | | | 290 | | | | | |
| GAC | TGC | CAG | AAG | CAT | GCT | GTC | ATT | GTG | TCT | GTC | ATC | AAC | AGC | TCC | ACC | 1204 |
| Asp | Cys | Gln | Lys | His | Ala | Val | Ile | Val | Ser | Val | Ile | Asn | Ser | Ser | Thr | |
| 295 | | | | 300 | | | | | 305 | | | | | 310 | | |
| TCC | ATA | TTT | GCC | AGC | ATT | GTC | ACC | TTC | TCC | ATC | TAT | GGC | TTC | AAG | GCC | 1252 |
| Ser | Ile | Phe | Ala | Ser | Ile | Val | Thr | Phe | Ser | Ile | Tyr | Gly | Phe | Lys | Ala | |
| | | | | 315 | | | | | 320 | | | | | 325 | | |
| ACC | TTC | AAC | TAT | GAA | AAC | TGC | TTA | AAC | AAG | GTG | ATT | CTG | CTG | CTG | ACC | 1300 |
| Thr | Phe | Asn | Tyr | Glu | Asn | Cys | Leu | Asn | Lys | Val | Ile | Leu | Leu | Leu | Thr | |
| | | | 330 | | | | | 335 | | | | | 340 | | | |
| AAT | TCT | TTT | GAC | CTT | GAA | GAT | GGC | TTT | CTG | ACA | GCC | AGC | AAC | CTG | GAG | 1348 |
| Asn | Ser | Phe | Asp | Leu | Glu | Asp | Gly | Phe | Leu | Thr | Ala | Ser | Asn | Leu | Glu | |
| | | 345 | | | | | 350 | | | | | 355 | | | | |
| GAG | GTG | AAG | GAC | TAC | CTG | GCA | TCT | ACT | TAC | CCA | AAC | AAG | TAC | AGT | GAA | 1396 |
| Glu | Val | Lys | Asp | Tyr | Leu | Ala | Ser | Thr | Tyr | Pro | Asn | Lys | Tyr | Ser | Glu | |
| | 360 | | | | | 365 | | | | | 370 | | | | | |
| GTG | TTC | CCA | CAC | ATT | AGA | AAC | TGC | AGC | TTG | GAA | TCA | GAG | CTG | AAC | ACG | 1444 |
| Val | Phe | Pro | His | Ile | Arg | Asn | Cys | Ser | Leu | Glu | Ser | Glu | Leu | Asn | Thr | |
| 375 | | | | 380 | | | | | 385 | | | | | 390 | | |
| GCT | GTC | CAA | GGC | ACA | GGC | CTG | GCC | TTC | ATC | GTC | TAC | GCT | GAG | GCC | ATT | 1492 |
| Ala | Val | Gln | Gly | Thr | Gly | Leu | Ala | Phe | Ile | Val | Tyr | Ala | Glu | Ala | Ile | |
| | | | | 395 | | | | | 400 | | | | | 405 | | |
| AAA | AAC | ATG | GAA | GTG | TCC | CAG | CTC | TGG | TCA | GTG | CTC | TAC | TTC | TTC | ATG | 1540 |
| Lys | Asn | Met | Glu | Val | Ser | Gln | Leu | Trp | Ser | Val | Leu | Tyr | Phe | Phe | Met | |
| | | | 410 | | | | | 415 | | | | | 420 | | | |
| CTG | CTG | ATG | CTG | GGA | ATG | GGG | AGC | ATG | CTT | GGA | AAT | ACA | GCG | GCC | ATC | 1588 |
| Leu | Leu | Met | Leu | Gly | Met | Gly | Ser | Met | Leu | Gly | Asn | Thr | Ala | Ala | Ile | |
| | | 425 | | | | | 430 | | | | | 435 | | | | |
| CTC | ACC | CCT | CTG | ACT | GAC | AGC | AAG | GTC | ATC | TCC | AGC | TAC | CTG | CCC | AAG | 1636 |
| Leu | Thr | Pro | Leu | Thr | Asp | Ser | Lys | Val | Ile | Ser | Ser | Tyr | Leu | Pro | Lys | |
| | 440 | | | | | 445 | | | | | 450 | | | | | |
| GAG | GCC | ATT | TCA | GGT | CTG | GTG | TGC | CTC | ATT | AAC | TGT | GCT | GTT | GGC | ATG | 1684 |
| Glu | Ala | Ile | Ser | Gly | Leu | Val | Cys | Leu | Ile | Asn | Cys | Ala | Val | Gly | Met | |
| 455 | | | | 460 | | | | | 465 | | | | | 470 | | |
| GTG | TTC | ACC | ATG | GAG | GCT | GGG | AAC | TAC | TGG | TTT | GAC | ATA | TTC | AAT | GAC | 1732 |
| Val | Phe | Thr | Met | Glu | Ala | Gly | Asn | Tyr | Trp | Phe | Asp | Ile | Phe | Asn | Asp | |
| | | | | 475 | | | | | 480 | | | | | 485 | | |

| | | | | | | | | | | | | | | | | |
|---|---|---|---|---|---|---|---|---|---|---|---|---|---|---|---|---|
| TAT | GCA | GCC | ACG | CTG | TCT | CTG | CTG | CTC | ATT | GTG | CTG | GTG | GAG | ACT | ATA | 1780 |
| Tyr | Ala | Ala | Thr 490 | Leu | Ser | Leu | Leu | Leu 495 | Ile | Val | Leu | Val | Glu 500 | Thr | Ile | |
| GCT | GTG | TGC | TAC | GTG | TAT | GGG | CTG | AGG | AGA | TTT | GAA | AGT | GAT | CTT | CGG | 1828 |
| Ala | Val | Cys 505 | Tyr | Val | Tyr | Gly | Leu 510 | Arg | Arg | Phe | Glu | Ser 515 | Asp | Leu | Arg | |
| GCC | ATG | ACT | GGC | CGG | CCC | CTC | AAC | TGG | TAC | TGG | AAG | GCC | ATG | TGG | GCT | 1876 |
| Ala | Met 520 | Thr | Gly | Arg | Pro | Leu | Asn 525 | Trp | Tyr | Trp | Lys 530 | Ala | Met | Trp | Ala | |
| TTT | GTG | AGC | CCA | CTG | CTC | ATC | ATC | GGC | CTC | TTT | ATC | TTC | TAC | CTG | AGT | 1924 |
| Phe 535 | Val | Ser | Pro | Leu | Leu 540 | Ile | Ile | Gly | Leu | Phe 545 | Ile | Phe | Tyr | Leu | Ser 550 | |
| GAC | TAC | ATC | CTC | ACG | GGA | ACG | CTG | CAG | TAC | CAA | GCC | TGG | GAT | GCT | ACT | 1972 |
| Asp | Tyr | Ile | Leu | Thr 555 | Gly | Thr | Leu | Gln | Tyr 560 | Gln | Ala | Trp | Asp | Ala 565 | Thr | |
| CAG | GGG | CAG | CTG | GTG | ACC | AAG | GAT | TAC | CCT | CCA | CAT | GCA | CTA | GCT | GTC | 2020 |
| Gln | Gly | Gln | Leu 570 | Val | Thr | Lys | Asp | Tyr 575 | Pro | Pro | His | Ala | Leu 580 | Ala | Val | |
| ATC | GGT | TTG | CTG | GTG | GCT | TCA | TCT | ACT | ATG | TGC | ATC | CCC | CTG | GTG | GCC | 2068 |
| Ile | Gly | Leu 585 | Leu | Val | Ala | Ser | Ser 590 | Thr | Met | Cys | Ile | Pro 595 | Leu | Val | Ala | |
| CTG | GGG | ACT | TTC | ATC | AGG | AAT | CGC | CTC | AAG | AGG | GGA | GGC | TCT | TCC | CCA | 2116 |
| Leu | Gly 600 | Thr | Phe | Ile | Arg | Asn 605 | Arg | Leu | Lys | Arg | Gly 610 | Gly | Ser | Ser | Pro | |
| GTG | GCC | TAAGAATGGA | CCTCCCAAAG | ACCGAAGTCA | GCCACTCTGT | TTCACAGTTA | | | | | | | | | | 2172 |
| Val | Ala 615 | | | | | | | | | | | | | | | |

```
CCACCTGCTG  GTGGGATCTT  CTTGGCTGGA  GTGCTGGTCT  GTGGCCTCCT  GAGTCTGTAT         2232
AGAAGATGAG  AGAGCTTAGC  AAAAGAAGAC  TGCCTTGGGG  AGGGGACCAC  ATCCCTTAGG         2292
AGGGGCCCTC  CATCCTCTGC  CGTCTGAAGG  TCATACCTTA  TAGCCTCTTT  GTCATCAAAG         2352
GTTAAGGCCA  GTATTGAAGA  TTGTTGTTTT  CTTGATTCTA  GAAAGTTCTA  GAATTTAAGG         2412
TAAACTGTCA  TTAGAAACTT  GACTGTAACT  CTAAGGAGCC  AAACAAGCAA  TTACATTTTT         2472
TTTATTGTTG  TTGTTGTTGT  TTAAAAGAAA  ACAAAATACT  AGAGGGTATT  TGCTTTTCAA         2532
CCAGTGTCAG  AGGTTTTGAA  GCATGAAAGG  TGACAAATTA  AATTTAATCT  AGCTCTTTTC         2592
TATAAAGTCA  CAATGAATGT  GCAATTTCTC  TGTTCCCTGA  CTACTCTCTA  TATGTTACCA         2652
GGATATAATA  GCCACTAAGA  GACTTTTTCT  GGGGTTCCAA  TGGACGTCAC  CTTTCTCTGA         2712
ATCTAAGGTT  CCTCACAGTG  GGCCAGGACC  AACCTCTCTA  CAACTCTAGA  CTGCACAAGG         2772
AATCTGAACA  GACACTCCCA  TCTCTAGGGT  TTCAGTGTCA  GATGCATCTA  TAAGGATACA         2832
AGTAACTCTA  ACTTTGCTAT  AAATATCACT  CGCGACCACC  TTCATTCACT  TCTGAATAAT         2892
AATGTTTTCT  AAAATGTATA  TAAATCACAC  AGAGCAGTGT  GTAGCTGAAA  ATACTCCATA         2952
TTTATGGCTG  TTATCCATGC  ACCATGTGAA  TATGTCTCTT  TTTTATCGTA  ATAAAGTGAA         3012
TCAAGGTTAT  CT                                                                 3024
```

( 2 ) INFORMATION FOR SEQ ID NO:2:

( i ) SEQUENCE CHARACTERISTICS:
        ( A ) LENGTH: 616 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

Met  Arg  Leu  Ala  Ile  Lys  Arg  Arg  Ala  Ser  Arg  Gly  Gln  Arg  Pro  Gly

|     |     |     |     |     |     |     |     |     |     |     |     |     |     |     |
| --- | --- | --- | --- | --- | --- | --- | --- | --- | --- | --- | --- | --- | --- | --- |
| 1 | | | | 5 | | | | | 10 | | | | | 15 |
| Pro | Asp | Glu | Lys<br>20 | Arg | Ala | Arg | Asp | Met<br>25 | Glu | Lys | Ala | Arg<br>30 | Pro | Gln | Trp |

Pro Asp Glu Lys Arg Ala Arg Asp Met Glu Lys Ala Arg Pro Gln Trp
            20              25              30

Gly Asn Pro Leu Gln Phe Val Phe Ala Cys Ile Ser Tyr Ala Val Gly
        35              40                  45

Leu Gly Asn Val Trp Arg Phe Pro Tyr Leu Cys Gln Met Tyr Gly Gly
    50                  55                  60

Gly Ser Phe Leu Val Pro Tyr Leu Ile Met Leu Ile Val Glu Gly Met
65              70              75                          80

Pro Leu Leu Tyr Leu Glu Leu Ala Val Gly Gln Arg Met Arg Gln Gly
            85              90                  95

Ser Ile Gly Ala Trp Arg Thr Ile Ser Pro Tyr Leu Ser Gly Val Gly
        100             105             110

Val Ala Ser Val Val Val Ser Phe Phe Leu Ser Met Tyr Tyr Asn Val
        115             120             125

Ile Asn Ala Trp Gly Phe Trp Tyr Leu Phe His Ser Phe Gln Asp Pro
    130             135             140

Leu Pro Trp Ser Val Cys Pro Leu Asn Ser Asn Arg Thr Gly Tyr Asp
145             150             155                         160

Glu Glu Cys Glu Lys Ala Ser Ser Thr Gln Tyr Phe Trp Tyr Arg Lys
            165             170                 175

Thr Leu Asn Ile Ser Pro Ser Ile Gln Glu Asn Gly Gly Val Gln Trp
            180             185                 190

Glu Pro Ala Leu Cys Leu Thr Leu Ala Trp Leu Met Val Tyr Leu Cys
        195             200             205

Ile Leu Arg Gly Thr Glu Ser Thr Gly Lys Val Val Tyr Phe Thr Ala
        210             215             220

Leu Met Pro Tyr Cys Val Leu Ile Ile Tyr Leu Val Arg Gly Leu Thr
225             230             235                         240

Leu His Gly Ala Thr Asn Gly Leu Met Tyr Met Phe Thr Pro Lys Ile
                245             250                 255

Glu Gln Leu Ala Asn Pro Lys Ala Trp Ile Asn Ala Ala Thr Gln Ile
            260             265             270

Phe Phe Ser Leu Gly Leu Gly Phe Gly Ser Leu Ile Ala Phe Ala Ser
        275             280             285

Tyr Asn Glu Pro Ser Asn Asp Cys Gln Lys His Ala Val Ile Val Ser
    290             295             300

Val Ile Asn Ser Ser Thr Ser Ile Phe Ala Ser Ile Val Thr Phe Ser
305             310             315                         320

Ile Tyr Gly Phe Lys Ala Thr Phe Asn Tyr Glu Asn Cys Leu Asn Lys
            325             330                 335

Val Ile Leu Leu Leu Thr Asn Ser Phe Asp Leu Glu Asp Gly Phe Leu
            340             345             350

Thr Ala Ser Asn Leu Glu Glu Val Lys Asp Tyr Leu Ala Ser Thr Tyr
        355             360             365

Pro Asn Lys Tyr Ser Glu Val Phe Pro His Ile Arg Asn Cys Ser Leu
    370             375             380

Glu Ser Glu Leu Asn Thr Ala Val Gln Gly Thr Gly Leu Ala Phe Ile
385             390             395                         400

Val Tyr Ala Glu Ala Ile Lys Asn Met Glu Val Ser Gln Leu Trp Ser
            405             410                 415

Val Leu Tyr Phe Phe Met Leu Leu Met Leu Gly Met Gly Ser Met Leu
            420             425             430

| | | | | | | | | | | | | | | |
|--|--|--|--|--|--|--|--|--|--|--|--|--|--|--|
| Gly | Asn | Thr 435 | Ala | Ala | Ile | Leu | Thr 440 | Pro | Leu | Thr | Asp | Ser 445 | Lys | Val | Ile |
| Ser | Ser 450 | Tyr | Leu | Pro | Lys | Glu 455 | Ala | Ile | Ser | Gly | Leu 460 | Val | Cys | Leu | Ile |
| Asn 465 | Cys | Ala | Val | Gly | Met 470 | Val | Phe | Thr | Met | Glu 475 | Ala | Gly | Asn | Tyr | Trp 480 |
| Phe | Asp | Ile | Phe | Asn 485 | Asp | Tyr | Ala | Ala | Thr 490 | Leu | Ser | Leu | Leu | Leu 495 | Ile |
| Val | Leu | Val | Glu 500 | Thr | Ile | Ala | Val | Cys 505 | Tyr | Val | Tyr | Gly | Leu 510 | Arg | Arg |
| Phe | Glu | Ser 515 | Asp | Leu | Arg | Ala | Met 520 | Thr | Gly | Arg | Pro | Leu 525 | Asn | Trp | Tyr |
| Trp | Lys 530 | Ala | Met | Trp | Ala | Phe 535 | Val | Ser | Pro | Leu | Leu 540 | Ile | Ile | Gly | Leu |
| Phe 545 | Ile | Phe | Tyr | Leu | Ser 550 | Asp | Tyr | Ile | Leu | Thr 555 | Gly | Thr | Leu | Gln | Tyr 560 |
| Gln | Ala | Trp | Asp | Ala 565 | Thr | Gln | Gly | Gln | Leu 570 | Val | Thr | Lys | Asp | Tyr 575 | Pro |
| Pro | His | Ala | Leu 580 | Ala | Val | Ile | Gly | Leu 585 | Leu | Val | Ala | Ser | Ser 590 | Thr | Met |
| Cys | Ile | Pro 595 | Leu | Val | Ala | Leu | Gly 600 | Thr | Phe | Ile | Arg | Asn 605 | Arg | Leu | Lys |
| Arg | Gly 610 | Gly | Ser | Ser | Pro | Val 615 | Ala | | | | | | | | |

DNA ENCODING A NOVEL MAMMALIAN TRANSPORTER HOMOLOGOUS TO NEUROTRANSMITTER TRANSPORTERS AND USES THEREOF

BACKGROUND OF THE INVENTION

Throughout this application various publications are referred to by partial citations within parenthesis. Full citations for these publications may be found at the end of the specification immediately preceding the claims. The disclosures of these publications, in their entireties, are hereby incorporated by reference into this application in order to more fully describe the state of the art to which this invention pertains.

Transporters throughout the body control the solute composition of the CSF, urine, plasma, and other extracellular fluids. In the brain, neurotransmitter transporters serve specialized functions related to the modulation of synaptic transmission. The recent cloning of genes encoding neurotransmitter transporters is facilitating the elucidation of the role of transport proteins in nervous system health and disease. The availability of cloned transporters provides the opportunity to define the pharmacological profiles of specific gene products, map their patterns of distribution, and make correlations with in vivo observations to better understand their biological functions.

Since the description of the primary structure of the first neurotransmitter transporter (the GABA transporter GAT-1; Guastella et al., 1990) at least 10 additional transporters with related sequences have been cloned (see Amara and Kuhar, 1993 for review), defining a new gene family. Members of this family typically exhibit from ~40% to ~70% overall amino acid identity with each other, and share a number of structural and functional features, including 12 predicted transmembrane domains, potential sites for glycosylation in extracellular domains, and dependence on sodium for transport activity. Transporters in this family include those for norepinephrine (Pacholczyk et al., 1991), serotonin (Blakely et al., 1991; Hoffman et al., 1991), dopamine (Kilty et al., 1991; Shimada et al., 1991), glycine (Smith et al., 1992a; Guastella et al., 1992; Liu et al., 1992b; Borowsky et al., 1993), GABA (Guastella et al., 1990; Clark et al., 1992; Borden et al., 1992; Liu et al., 1993), betaine (Yamauchi et al., Lopez-Corcuera et al., 1992), taurine/β-alanine (Uchida et al., 1992; Smith et al., 1992; Liu et al., 1992), L-proline (Fremeau et al., 1992), and creatine (Guimbal and Kilimann, 1993). Each of these transporters has been found in the brain and nearly all have substrates that are either neuroregulators, osmoregulators, or both, reinforcing the concept that molecules with similar structures often have similar functions.

In addition to those described above, several transporters have been cloned that exhibit significant amino acid identity with the neurotransmitter transporters, but whose endogenous substrates have not yet been identified (Uhl et al., 1992; Liu et al., 1993a). We describe here the cloning and localization of a novel "orphan" transporter from rat brain, rB21a, whose structural homology with neurotransmitter transporters indicates it is a member of this gene family. Its presence in the brain further suggests that its endogenous substrate may be neuroactive; in fact, it has been suggested that identifying the substrates of "orphan" transporters could reveal previously undescribed neurotransmitter systems (Uhl, 1992). The cloning of rB21a provides the means to determine its functions in the nervous system. As a novel transporter homologous to neurotransmitter transporters, rB21a may be useful as a target for the development of therapeutic agents for neurological and psychiatric disorders.

SUMMARY OF THE INVENTION

This invention provides an isolated nucleic acid molecule encoding a mammalian rB21a transporter. In one embodiment of this invention, the nucleic acid molecule comprises a plasmid designated pcEVX-rB21a (ATCC Accession No. 75609, deposited Nov. 5, 1993).

This invention provides a nucleic acid probe comprising a nucleic acid molecule of at least 15 nucleotides capable of specifically hybridizing with a unique sequence included within the sequence of a nucleic acid molecule encoding a mammalian rB21a transporter.

This invention further provides an antisense oligonucleotide having a sequence capable of binding specifically to an mRNA molecule encoding a mammalian rB21a transporter so as to prevent translation of the mRNA molecule.

A monoclonal antibody directed to a mammalian rB21a transporter is provided by this invention.

This invention further provides a pharmaceutical composition comprising an amount of a substance effective to alleviate the abnormalities resulting from overexpression of a mammalian rB21a transporter and a pharmaceutically acceptable carrier as well as a pharmaceutical composition comprising an amount of a substance effective to alleviate abnormalities resulting from underexpression of rB21a transporter and a pharmaceutically acceptable carrier.

This invention provides a transgenic, nonhuman mammal comprising the isolated nucleic acid molecule encoding the mammalian rB21a transporter either through homologous recombination with the nonhuman mammal's endogenous gene encoding the rB21a transporter or in tandem with the nonhuman mammal's endogenous gene encoding the rB21a transporter.

This invention also provides a transgenic, nonhuman mammal whose genome comprises either a gene encoding the rB21a transporter that is so modified as to be incapable of being expressed or an antisense DNA complementary to DNA encoding a mammalian rB21a transporter so positioned within such genome as to be transcribed into antisense mRNA complementary to mRNA encoding the rB21a transporter capable of specifically hybridizing to mRNA encoding the rB21a transporter and therefore reduce the translation of the mRNA encoding the rB21a transporter.

This invention provides a method of screening drugs to identify drugs which specifically interact with, and bind to, the mammalian rB21a transporter which comprises contacting a mammalian cell comprising an isolated DNA molecule encoding the rB21a transporter under conditions suitable for the expression of a mammalian rB21a transporter with a plurality of drugs, determining those drugs which bind to the mammalian cell, and thereby identifying drugs which specifically interact with, and bind to, a mammalian rB21a transporter.

This invention also provides a method of determining the physiological effects of expressing varying levels of mammalian rB21a transporter which comprises producing a transgenic nonhuman animal whose levels of mammalian rB21a transporter expression are varied by use of an inducible promoter which regulates the mammalian rB21a transporter expression.

This invention further provides a method of determining the physiological effects of expressing varying levels of mammalian rB21a transporter which comprises producing a panel of transgenic nonhuman animals each expressing a different amount of mammalian rB21a transporter.

This invention provides a method for determining whether a substrate not known to be capable of binding to a rB21a transporter can bind to a rB21a transporter which comprises contacting a mammalian cell comprising an isolated DNA molecule encoding the rB21a transporter with the substrate under conditions permitting binding of substrates known to bind to a transporter, detecting the presence of any of the substrate bound to the rB21a transporter, and thereby determining whether the substrate binds to the rB21a transporter.

BRIEF DESCRIPTION OF THE FIGURES

FIG. 1. Nucleotide Sequence and Deduced Amino Acid Sequence of the Rat rB21a Transporter. Nucleotides are presented in the 5' to 3' orientation and the coding region is numbered starting from the putative initiating methionine and ending in the termination codon. Deduced amino acid sequence by translation of a long open reading frame is shown using one-letter symbols.

FIG. 2. Alignment of the Rat rB21a Deduced Amino Acid Sequence with the GAT-2, Glycine, Taurine, and Norepinephrine Transporters. The twelve putative transmembrane domains (I-XII) are bracketed. GAT-2 represents the rat GABA transporter (Borden et al., 1992); Glycine represents the rat glycine transporter (Smith et al., 1992); Taurine represents the rat taurine transporter (Smith et al., 1992a); Norepi represents the human norepinephrine transporter (Pacholczyk et al., 1991).

FIG. 4. Regional Brain Localization of mRNA Encoding rB21a by Northern Blot Analysis. Poly A+ RNAs (5 µg) from rat brain regions were separated by formaldehyde/agarose gel electrophoresis, blotted to nylon membranes, and hybridized at high stringency with $^{32}$P-labeled rB21a transporter cDNA. The locations of RNA size markers are indicated in kilobases. The hybridizing transcript is ~3 kb; the autoradiogram was exposed for 4 days.

DETAILED DESCRIPTION OF THE INVENTION

Figure 3:
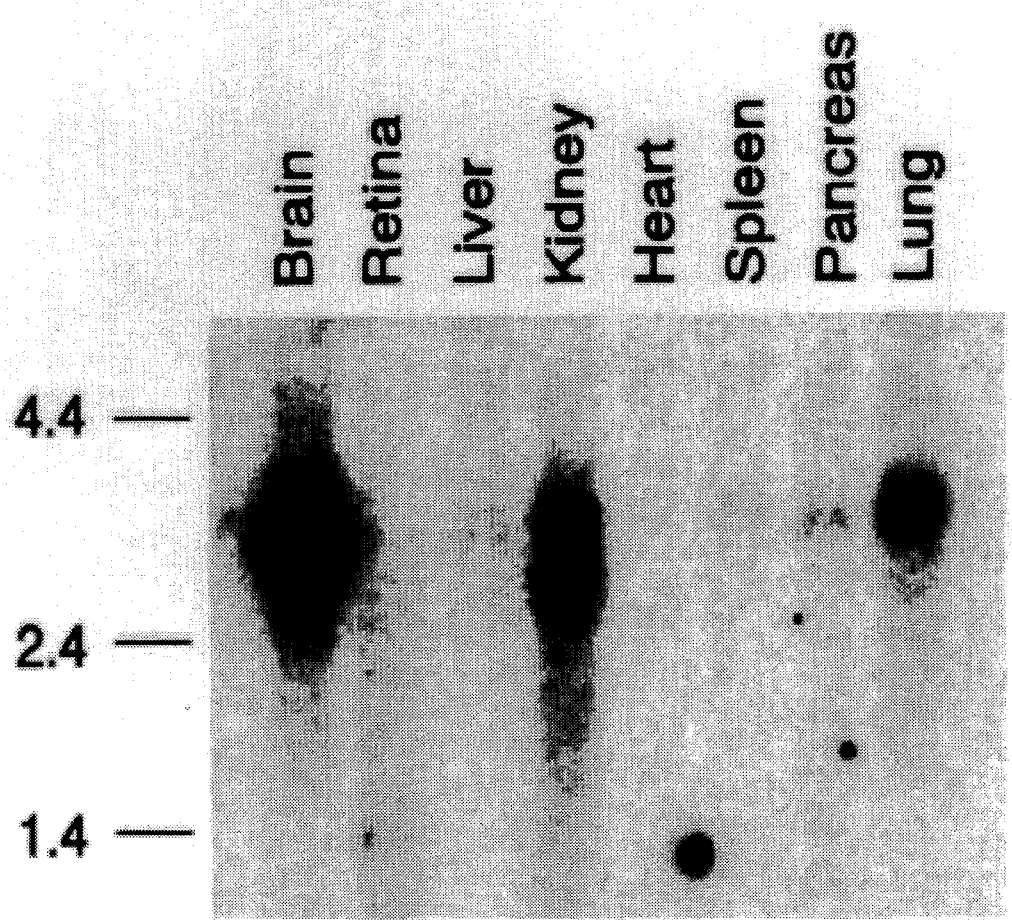
FIG. 3. Tissue Localization of rB21a by Northern Blot Analysis. Poly A+ RNAs (5 µg) from rat tissues were separated by formaldehyde/agarose gel electrophoresis, blotted to nylon membranes, and hybridized at high stringency with $^{32}$P-labeled rB21a transporter cDNA. The locations of RNA size markers are indicated in kilobases. The hybridizing transcripts are ~3 kb and ~2.6 kb; the autoradiogram was exposed for 22 days.
Figure 5A:
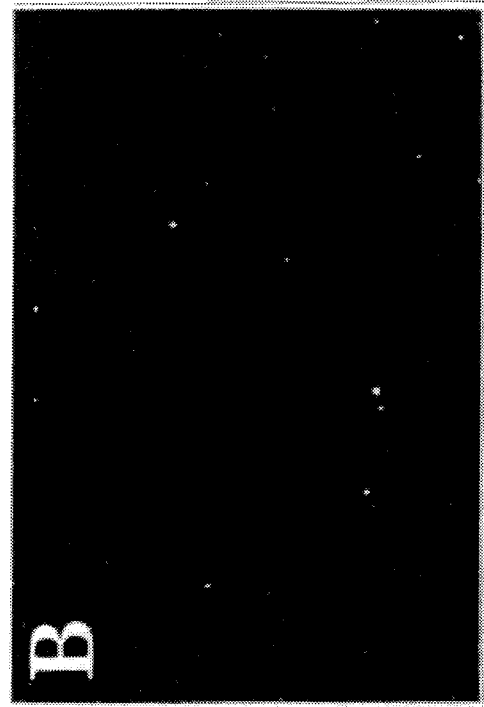
FIG. 5. Detection of the rB21a transporter mRNA in the Rat CNS and Kidney by In Situ Hybridization. A-B. Black and white reversal of film autoradiograms of coronal rat brain sections hybridized with $^{35}$S-labeled (A) antisense ⅞ loop oligonucleotide, and (B) sense oligonucleotide, illustrating the transporter's localization in the leptomeninges. C-F. Liquid emulsion autoradiograph of the rB21a transporter mRNA in leptomeningeal cells covering (C) the telencephalon in the area adjacent to the third ventricle (v), (D) the cerebellum and brain stem, and (E, F) the ventral aspect of the brain. Note the lack of hybridization signal over cells of the choroid plexus (cp) in C and over smooth muscle cells of a blood vessel (bv) in E. G-H. Kidney distribution of the rB21a transporter mRNA. (G) The hybridization observed with the rB21a antisense probe is largely limited to the outer zone of the medulla (white arrow) while there is no hybridization observed with the sense probe (H).
Figure 5B:
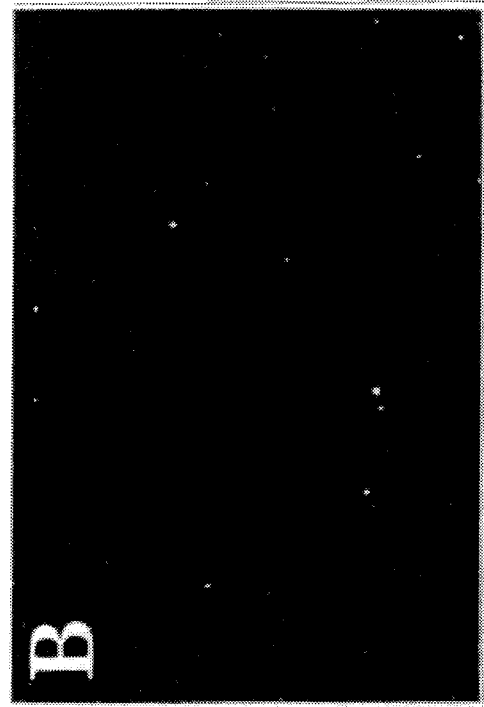
Figure 5C:
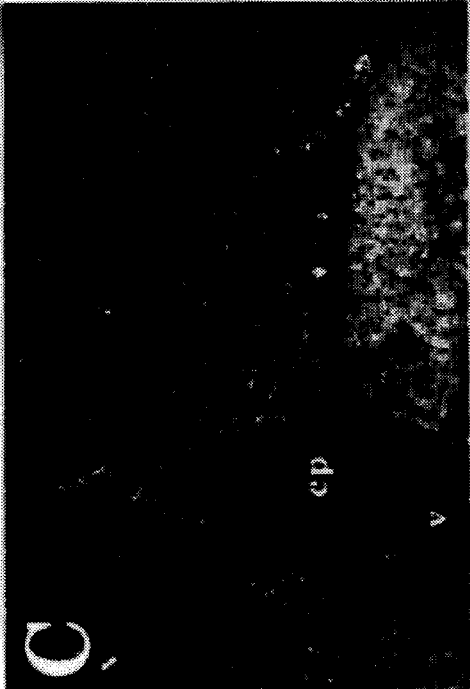
Figure 5D:
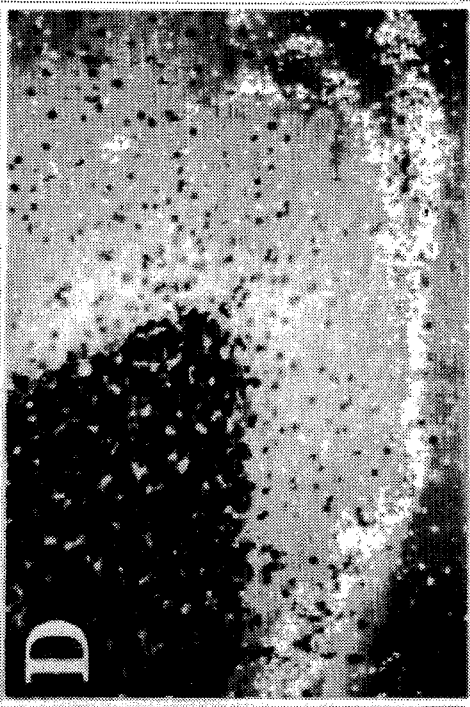
Figure 5F:
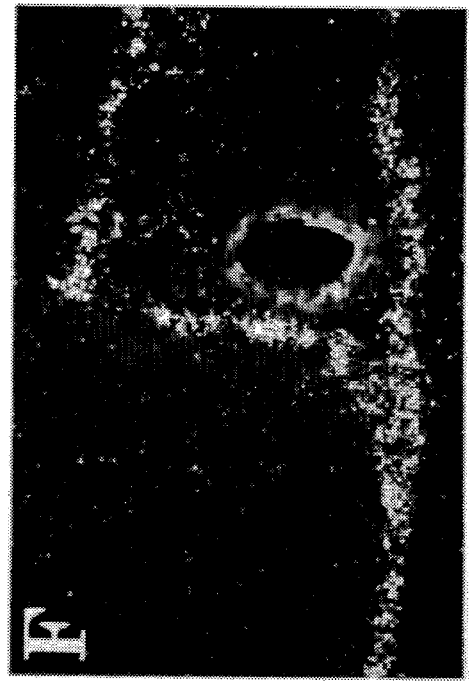
Figure 5H:
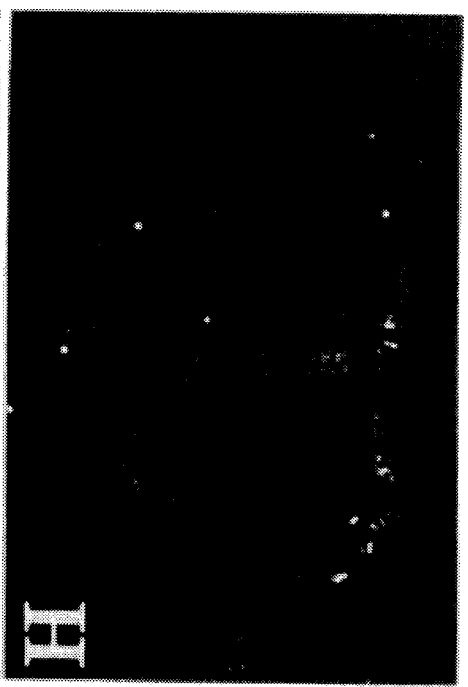
Figure 5E:
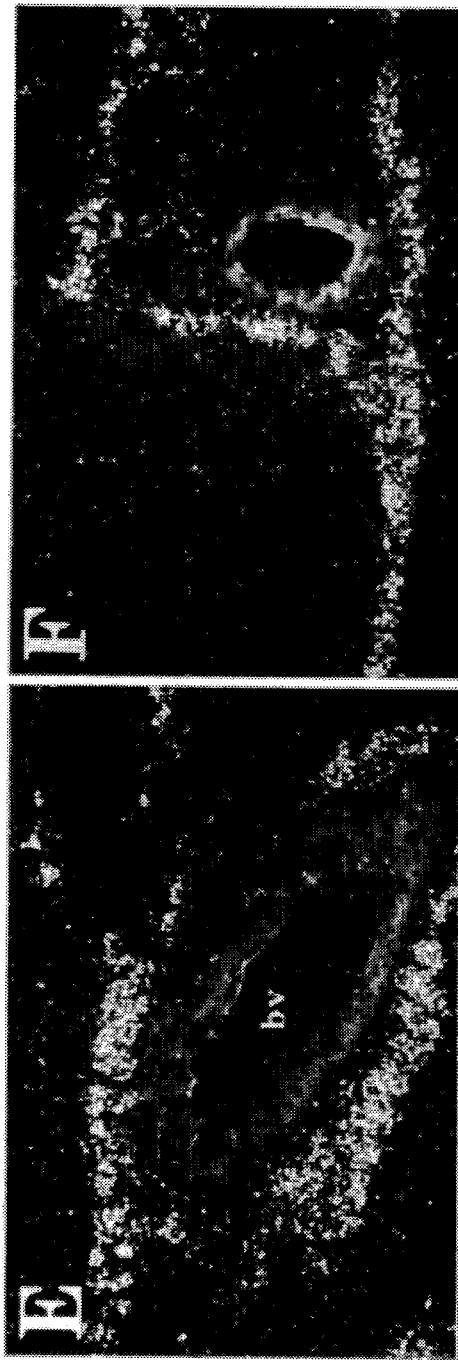
Figure 5G:

This invention provides an isolated nucleic acid molecule encoding a mammalian rB21a transporter. As used herein, the term "isolated nucleic acid molecule" means a non-naturally occurring nucleic acid molecule that is, a molecule in a form which does not occur in nature. Examples of such an isolated nucleic acid molecule are an RNA, cDNA, or isolated genomic DNA molecule encoding a mammalian rB21a transporter. As used herein, "rB21a transporter" means a molecule which has substantially the same amino acid sequence as described in FIG. 1 (Seq. I.D. 2). One embodiment of this invention is an isolated rat nucleic acid molecule encoding a rB21a transporter. Such a molecule may have coding sequences substantially the same as the coding sequences shown in FIG. 1 (Seq I.D. No. 1). The DNA molecule of FIG. 1 (Seq. I.D. No. 1) encodes the sequence of the mammalian rB21a transporter gene. One means of isolating a mammalian rB21a transporter is to probe a mammalian genomic library with a natural or artificially designed DNA probe, using methods well known in the art. In one embodiment of this invention, the mammalian rB21a transporter and the nucleic acid molecules encoding them are isolated from a rat cDNA library. DNA and cDNA molecules which encode mammalian rB21a transporter are used to obtain complementary genomic DNA, cDNA or RNA from human, mammalian or other animal sources, or to isolate related cDNA or genomic clones by the screening of cDNA or genomic libraries, by methods described in more detail below. Transcriptional regulatory elements from the 5' untranslated region of the isolated clone, and other stability, processing, transcription, translation, and tissue specificity determining regions from the 3' and 5' untranslated regions of the isolated gene are thereby obtained.

This invention provides an isolated nucleic acid molecule encoding a mammalian rB21a transporter which has been so mutated as to be incapable of being expressed. An example of a mutated nucleic acid molecule provided by this invention is an isolated nucleic acid molecule which has an in-frame stop codon inserted into the coding sequence such that the transcribed RNA is not translated into protein.

This invention further provides a cDNA molecule encoding a mammalian rB21a transporter, wherein the cDNA molecule has a coding sequence substantially the same as the coding sequence shown in FIG. 1 (Sequence I.D. No. 1). This molecule and its equivalents was obtained by the means described above.

This invention also provides a vector comprising an isolated nucleic acid molecule such as DNA, RNA, or cDNA, encoding a mammalian rB21a transporter. Examples of vectors are viruses such as bacteriophages (including but not limited to phage lambda), animal viruses (including but not limited to baculovirus, Herpes virus, and Murine Leukemia virus), cosmids, plasmids (such as pUC18, available from Pharmacia, Piscataway, N.J.), and other recombination vectors. Nucleic acid molecules are inserted into vector genomes by methods well known to those skilled in the art.

Examples of such plasmids are plasmids comprising cDNA having a coding sequence substantially the same as: the coding sequence shown in FIG. 1 (Seq. I.D. No. 1) and designated clone pcEXV-rB21a deposited under ATCC Accession No. 75609, deposited Nov. 5, 1993. Alternatively, to obtain these vectors, insert and vector DNA can both be exposed to a restriction enzyme to create complementary ends on both molecules which base pair with each other and are then ligated together with a ligase. Alternatively, linkers can be ligated to the insert DNA which correspond to a restriction site in the vector DNA, which is then digested with the restriction enzyme which cuts at that site. Other means are also available.

This invention also provides vectors comprising a DNA molecule encoding a mammalian rB21a transporter, adapted for expression in a bacterial cell, a yeast cell, an insect cell, or a mammalian cell which additionally comprise the regulatory elements necessary for expression of the DNA in the bacterial, yeast, insect, or mammalian cells operatively linked to the DNA encoding a mammalian rB21a transporter as to permit expression thereof. DNA having coding sequences substantially the same as the coding sequence shown in FIG. 1 may usefully be inserted into the vectors to express the transporter. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Maniatis, et al., Molecular Cloning, Cold Spring Harbor Laboratory, 1982). Similarly, a eukaryotic expression vector includes a heterologous or homologous promoter for RNA polymerase II, a downstream polyadenylation signal, the start codon AUG, and a termination codon for detachment of the ribosome. Furthermore, an insect expression vector such as baculovirus AcMNPV uses the strong viral expression signals for the virus' polyhedrin gene to drive transcription of the recombinant gene. Such vectors may be obtained commercially or assembled from the sequences described by methods well known in the art, for example the methods described above for constructing vectors in general. Expression vectors are useful to produce cells that express the transporter. Certain uses for such cells are described in more detail below.

In one embodiment of this invention a plasmid is adapted for expression in a bacterial, yeast, insect, or, in particular, a mammalian cell wherein the plasmid comprises a DNA molecule encoding a mammalian rB21a transporter and the regulatory elements necessary for expression of the DNA in the bacterial, yeast, insect or mammalian cell so located relative to the DNA encoding a mammalian as to permit expression thereof. Suitable plasmids may include, but are not limited to plasmids adapted for expression in a mammalian cell, e.g., pcEXV-3. Examples of such plasmids adapted for expression in a mammalian cell are plasmids comprising cDNA having coding sequences substantially the same as the coding sequence shown in FIG. 1 and the regulatory elements necessary for expression of the DNA in the mammalian cell. This plasmid has been designated pcEXV-rB21a and deposited under ATCC Accession No. 75609, deposited Nov. 5, 1993.

Those skilled in the art will readily appreciate that numerous plasmids adapted for expression in a mammalian cell which comprise DNA encoding a mammalian rB21a transporter and the regulatory elements necessary to express such DNA in the mammalian cell may be constructed utilizing existing plasmids and adapted as appropriate to contain the regulatory elements necessary to express the DNA in the mammalian cell. The plasmids may be constructed by the methods described above for expression vectors and vectors in general, and by other methods well known in the art.

The deposit discussed supra was made pursuant to, and in satisfaction of, the provisions of the Budapest Treaty on the International Recognition of the Deposit of Microorganisms for the Purpose of Patent Procedure with the American Type Culture Collection (ATCC), 12301 Parklawn Drive, Rockville, Md. 20852.

This invention provides a mammalian cell comprising a DNA molecule encoding a mammalian rB21a transporter, such as a mammalian cell comprising a plasmid adapted for expression in a mammalian cell, which comprises a DNA molecule encoding a mammalian rB21a transporter and the regulatory elements necessary for expression of the DNA in the mammalian cell operatively linked to the DNA encoding a mammalian transporter as to permit expression thereof. Numerous mammalian cells may be used as hosts, including, but not limited to, the mouse fibroblast cell NIH3T3, CHO cells, HeLa cells, Ltk$^-$ cells, Cos cells, etc. Expression plasmids such as that described supra may be used to transfect mammalian cells by methods well known in the art such as calcium phosphate precipitation, or DNA encoding these transporters may be otherwise introduced into mammalian cells, e.g., by microinjection, to obtain mammalian cells which comprise DNA, e.g., cDNA or a plasmid, encoding a rB21a transporter.

This invention provides a nucleic acid probe comprising a nucleic acid molecule of at least 15 nucleotides capable of specifically hybridizing with a unique sequence included within the sequence of a nucleic acid molecule comprising the gene encoding the mammalian rB21a transporter and its noncoding 3' and 5' nucleotides as shown in FIG. 1. As used herein, the phrase "specifically hybridizing" means the ability of a nucleic acid molecule to recognize a nucleic acid sequence complementary to its own and to form double-helical segments through hydrogen bonding between complementary base pairs. As used herein, a "unique sequence" is a sequence specific to only the nucleic acid molecules encoding the rB21a transporter. Nucleic acid probe technology is well known to those skilled in the art who will readily appreciate that such probes may vary greatly in length and may be labeled with a detectable label, such as a radioisotope or fluorescent dye, to facilitate detection of the probe. Detection of nucleic acid molecules encoding mammalian rB21a transporter is useful as a diagnostic test for any disease process in which levels of expression of the corresponding rB21a transporter are altered. DNA probe molecules are produced by insertion of a DNA molecule which encodes mammalian rB21a transporter or fragments thereof into suitable vectors, such as plasmids or bacteriophages, followed by insertion into suitable bacterial host cells and replication and harvesting of the DNA probes, all using methods well known in the art. For example, the DNA may be extracted from a cell lysate using phenol and ethanol, digested with restriction enzymes corresponding to the insertion sites of the DNA into the vector (discussed above), electrophoresed, and cut out of the resulting gel. Examples of such DNA molecules are shown in FIG. 1. The probes are useful for 'in situ' hybridization or in order to locate tissues which express this gene family, or for other hybridization assays for the presence of these genes or their mRNA in various biological tissues. In addition, synthesized oligonucleotides (produced by a DNA synthesizer) complementary to the sequence of a DNA molecule which encodes a mammalian rB21a transporter are useful as probes for this gene, for its associated mRNA, or for the isolation of related genes by homology screening of genomic or cDNA libraries, or by the use of amplification techniques such as the Polymerase Chain Reaction.

This invention provides an antisense oligonucleotide having a sequence capable of specifically hybridizing with any sequences of an mRNA molecule which encodes a mammalian rB21a transporter so as to prevent translation of the mammalian rB21a transporter. As used herein, the phrase "specifically hybridizing" means the ability of an antisense oligonucleotide to recognize a nucleic acid sequence complementary to its own and to form double-helical segments through hydrogen bonding between complementary base pairs. The antisense oligonucleotide may have a sequence capable of binding specifically with any sequences of the cDNA molecules whose sequences are shown in FIG. 1. A particular example of an antisense oligonucleotide is an antisense oligonucleotide comprising chemical analogues of nucleotides. The oligonucleotide may be coupled to a substance which inactivates mRNA, such as a ribozyme.

This invention also provides a pharmaceutical composition comprising an effective amount of the oligonucleotide described above effective to reduce expression of a mammalian rB21a transporter by passing through a cell membrane and binding specifically with mRNA encoding a mammalian rB21a transporter in the cell so as to prevent its translation and a pharmaceutically acceptable hydrophobic carrier capable of passing through a cell membrane. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The pharmaceutically acceptable hydrophobic carrier capable of passing through cell membranes may also comprise a structure which binds to a transporter specific for a selected cell type and is thereby taken up by cells of the selected cell type. The structure may be part of a protein known to bind a cell-type specific transporter, for example-an insulin molecule, which would target pancreatic cells. DNA molecules having coding sequences substantially complementary to the coding sequence shown in FIG. 1 may be used as the oligonucleotides of the pharmaceutical composition.

This invention also provides an isolated protein which is a mammalian rB21a transporter. In one embodiment of this invention, the protein is a rat rB21a transporter protein having an amino acid sequence substantially similar to the amino acid sequence shown in FIG. 1 (Seq. I.D. Nos. 2). As used herein, the term "isolated protein" is intended to encompass a protein molecule free of other cellular components. One means for obtaining isolated rB21a transporter is to express DNA encoding the transporter in a suitable host, such as a bacterial, yeast, insect, or mammalian cell, using methods well known to those skilled in the art, and recovering the transporter protein after it has been expressed in such a host, again using methods well known in the art. The transporter may also be isolated from cells which express it, in particular from cells which have been transfected with the expression vectors described below in more detail.

This invention also provides an isolated unique polypeptide fragment of the mammalian rB21a transporter protein. As used herein, the term "unique polypeptide fragment" encompasses any polypeptide with substantially the same amino acid sequence as any unique amino acid sequence as shown in FIG. 1 (Sequence ID No. 2). One means for obtaining an isolated polypeptide fragment of a mammalian rB21a transporter protein is to treat isolated rB21a transporter protein with commercially available peptidases and then separate the polypeptide fragments using methods well known to those skilled in the art.

Polypeptide fragments are often useful as antigens used to induce an immune response and subsequently generate antibodies against the polypeptide fragment and possibly the whole polypeptide which in this case is the rB21a transporter protein.

This invention provides an antibody directed to the mammalian rB21a transporter. This antibody may comprise, for example, a monoclonal antibody directed to an epitope of a mammalian rB21a transporter present on the surface of a cell, the epitope having an amino acid sequence substantially the same as an amino acid sequence for a cell surface epitope of the mammalian rB21a transporter included in the amino acid sequence shown in FIG. 1. Amino acid sequences may be analyzed by methods well known to those skilled in the art to determine whether they produce hydrophobic or hydrophilic regions in the proteins which they build. In the case of cell membrane proteins, hydrophobic regions are well known to form the part of the protein that is inserted into the lipid bilayer which forms the cell membrane, while hydrophilic regions are located on the cell surface, in an aqueous environment. Therefore antibodies to the hydrophilic amino acid sequences shown in FIG. 1 will bind to a surface epitope of a mammalian rB21a transporter, as described. Antibodies directed to mammalian rB21a transporter may be polyclonal or monoclonal and are prepared using methods well known in the art. For example, monoclonal antibodies are prepared using hybridoma technology by fusing antibody producing B cells from immunized animals with myeloma cells and selecting the resulting hybridoma cell line producing the desired antibody. Cells such as NIH3T3 cells or Ltk⁻ cells may be used as immunogens to raise such an antibody. Alternatively, synthetic peptides may be prepared using commercially available machines and the amino acid sequences shown in FIG. 1. As a still further alternative, DNA, such as a cDNA or a fragment thereof, may be cloned and expressed and the resulting polypeptide recovered and used as an immunogen. These antibodies are useful to detect the presence of mammalian transporters encoded by the isolated DNA, or to inhibit the function of the rB21a transporter either in cells in vitro, in living animals, in humans, or in biological tissues or fluids isolated from animals or humans.

This invention also provides a pharmaceutical composition which comprises an effective amount of an antibody directed to an epitope of the mammalian rB21a transporter, effective to block binding of naturally occurring substrates to the rB21a transporter, and a pharmaceutically acceptable carrier. A monoclonal antibody directed to an epitope of a mammalian rB21a transporter present on the surface of a cell which has an amino acid sequence substantially the same as an amino acid sequence for a cell surface epitope of the mammalian rB21a transporter included in the amino acid sequence shown in FIG. 1 is useful for this purpose.

This invention also provides a method of treating abnormalities in a subject which are alleviated by reduction of expression of a mammalian rB21a transporter which comprises administering to the subject an effective amount of the pharmaceutical composition described above effective to block binding of naturally occurring substrates to the transporter and thereby alleviate abnormalities resulting from overexpression of a mammalian rB21a transporter. Binding of the antibody to the rB21a transporter prevents the transporter from functioning, thereby neutralizing the effects of overexpression. The monoclonal antibodies described above are both useful for this purpose. Some examples of abnormal conditions possibly associated with rB21a transporter activity are migraine headaches, and brain swelling after injury, hypoxia, seizures, and stroke.

This invention provides methods of detecting the presence of a mammalian rB21a transporter on the surface of a cell which comprises contacting the cell with an antibody directed to the mammalian rB21a transporter, under conditions permitting binding of the antibody to the transporter, detecting the presence of the antibody bound to the cell, and thereby the presence of the mammalian rB21a transporter on the surface of the cell. Such methods are useful for determining whether a given cell is defective in expression of rB21a transporters on the surface of the cell. Bound antibodies are detected by methods well known in the art, for example by binding fluorescent markers to the antibodies and examining the cell sample under a fluorescence microscope to detect fluorescence on a cell indicative of antibody binding. The monoclonal antibodies described above are useful for this purpose.

This invention also provides a method of treating abnormalities which are alleviated by reduction of expression of a mammalian rB21a transporter. This method comprises administering to a subject an effective amount of the pharmaceutical composition antisense oligonucleotides having a sequence capable of specifically hybridizing to an mRNA molecule encoding the rB21a transporter and thereby prevent translation of said mRNA as described above effective to reduce expression of the mammalian rB21a transporter in the subject. This invention also provides a method of treating abnormalities which are alleviated by reduction of expression of a mammalian rB21a transporter. Some examples of abnormal conditions possibly associated with rB21a transporter activity are migraine headaches, and brain swelling after injury, hypoxia, seizures, and stroke.

Antisense oligonucleotide pharmaceutical compositions as described herein inhibit translation of mRNA encoding the mammalian rB21a transporter. Synthetic antisense oligonucleotides, or other antisense chemical structures are designed to bind to mRNA encoding the rB21a transporter and inhibit translation of the mRNA and are useful as drugs to inhibit expression of mammalian rB21a transporter genes in patients. This invention provides a means to therapeutically alter levels of expression of mammalian rB21a transporter by the use of a synthetic antisense oligonucleotide drug (SAOD) which inhibits translation of mRNA encoding the transporter. Synthetic antisense oligonucleotides, or other antisense chemical structures designed to recognize and selectively bind to mRNA, are constructed to be complementary to portions of the nucleotide sequences shown in FIG. 1 of DNA, RNA or of chemically modified, artificial nucleic acids. The SAOD is designed to be stable in the blood stream for administration to patients by injection, or in laboratory cell culture conditions, for administration to cells removed from the patient. The SAOD is designed to be capable of passing through cell membranes in order to enter the cytoplasm of the cell by virtue of physical and chemical properties of the SAOD which render it capable of passing through cell membranes (e.g., by designing small, hydrophobic SAOD chemical structures) or by virtue of specific transport systems in the cell which recognize and transport the SAOD into the cell. In addition, the SAOD can be designed for administration only to certain selected cell populations by targeting the SAOD to be recognized by specific cellular uptake mechanisms which bind and take up the SAOD only within certain selected cell populations. For example, the SAOD may be designed to bind to a transporter found only in a certain cell type, as discussed above. The SAOD is also designed to recognize and selectively bind to the target mRNA sequence, which may correspond to a sequence contained within the sequences shown in FIG. 1 by virtue of complementary base pairing to the mRNA. Finally, the SAOD is designed to inactivate the target mRNA sequence by any of three mechanisms: 1) by binding to the target mRNA and thus inducing degradation of the mRNA by intrinsic cellular mechanisms such as RNAse I digestion, 2) by inhibiting translation of the mRNA target by interfering with the binding of translation-regulating factors or of ribosomes, or 3) by inclusion of other chemical structures, such as ribozyme sequences or reactive chemical groups, which either degrade or chemically modify the target mRNA. Synthetic antisense oligonucleotide drugs have been shown to be capable of the properties described above when directed against mRNA targets (J. S. Cohen, Trends in Pharm. Sci. 10, 435 (1989); H. M. Weintraub, Sci. Am. January (1990) p. 40). In addition, coupling of ribozymes to antisense oligonucleotides is a promising strategy for inactivating target mRNA (N. Sarver et al., Science 247, 1222 (1990)). An SAOD serves as an effective therapeutic agent if it is designed to be administered to a patient by injection, or if the patient's target cells are removed, treated with the SAOD in the laboratory, and replaced in the patient. In this manner, an SAOD serves as a therapy to reduce rB21a transporter expression in particular target cells of a patient, in any clinical condition which may benefit from reduced expression of the mammalian rB21a transporter.

This invention provides a transgenic nonhuman mammal expressing DNA encoding a mammalian rB21a transporter. This invention also provides a transgenic nonhuman mammal expressing DNA encoding a mammalian rB21a transporter so mutated as to be incapable of expressing native rB21a transporter. This invention further provides a transgenic nonhuman mammal whose genome comprises DNA encoding a mammalian rB21a transporter so placed as to be transcribed into antisense mRNA which is complementary to mRNA encoding a rB21a transporter and which hybridizes to mRNA encoding a rB21a transporter thereby reducing its translation. The DNA may additionally comprise an inducible promoter or additionally comprise tissue specific regulatory elements, so that expression can be induced, or restricted to specific cell types. Examples of DNA are DNA or cDNA molecules having a coding sequence substantially the same as the coding sequences shown in FIG. 1. An example of a transgenic animal is a transgenic mouse. Examples of tissue specificity-determining regions are the metallothionein promoter (Low, M. J., Lechan, R. M., Hammer, R. E. et al. Science 231:1002–1004 (1986)) and the L7 promotor (Oberdick, J., Smeyne, R. J., Mann, J. R., Jackson, S. and Morgan, J. I. Science 248:223–226 (1990)).

Animal model systems which elucidate the physiological and behavioral roles of mammalian transporters are produced by creating transgenic animals in which the expression of a transporter is either increased or decreased, or the amino acid sequence of the expressed transporter protein is altered, by a variety of techniques. Examples of these techniques include, but are not limited to: 1) Insertion of normal or mutant versions of DNA encoding a mammalian transporter or homologous animal versions of these genes, by microinjection, retroviral infection or other means well known to those skilled in the art, into appropriate fertilized embryos in order to produce a transgenic animal (Hogan B. et al. Manipulating the Mouse Embryo, A Laboratory Manual, Cold Spring Harbor Laboratory (1986)) or, 2)

Homologous recombination (Capecchi M. R. Science 244:1288–1292 (1989); Zimmer, A. and Gruss, P. Nature 338:150–153 (1989)) of mutant or normal, human or animal versions of these genes with the native gene locus in transgenic animals to alter the regulation of expression or the structure of these transporters. The technique of homologous recombination is well known in the art. It replaces the native gene with the inserted gene and so is useful for producing an animal that cannot express native transporter but does express, for example, an inserted mutant transporter, which has replaced the native transporter in the animal's genome by recombination, resulting in underexpression of the transporter. Microinjection adds genes to the genome, but does not remove them, and so is useful for producing an animal which expresses its own and added transporters, resulting in overexpression of the transporter.

One means available for producing a transgenic animal, with a mouse as an example, is as follows: Female mice are mated, and the resulting fertilized eggs are dissected out of their oviducts. The eggs are stored in an appropriate medium such as M2 medium (Hogan B. et al. Manipulating the Mouse Embryo, A Laboratory Manual, Cold Spring Harbor Laboratory (1986)). DNA or cDNA encoding a mammalian transporter is purified from a vector (such as pcEXV-rB21a) by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

Since the normal action of transporter-specific drugs is to activate or to inhibit the transporter, the transgenic animal model systems described above are useful for testing the biological activity of drugs directed against the rB21a transporter even before such drugs become available. These animal model systems are useful for predicting or evaluating possible therapeutic applications of drugs which activate or inhibit the mammalian rB21a transporter by inducing or inhibiting expression of the native or trans-gene and thus increasing or decreasing expression of normal or mutant rB21a transporter in the living animal. Thus, a model system is produced in which the biological activity of drugs directed against the mammalian rB21a transporter are evaluated before such drugs become available. The transgenic animals which over or under produce the transporter indicate by their physiological state whether over or under production of the transporter is therapeutically useful. It is therefore useful to evaluate drug action based on the transgenic model system. One use is based on the fact that it is well known in the art that a drug such as an antidepressant acts by blocking neurotransmitter uptake, and thereby increases the amount of neurotransmitter in the synaptic cleft. The physiological result of this action is to stimulate the production of less transporter by the affected cells, leading eventually to underexpression. Therefore, an animal which underexpresses transporter is useful as a test system to investigate whether the actions of such drugs which result in under expression are in fact therapeutic. Another use is that if overexpression is found to lead to abnormalities, then a drug which downregulates or acts as an antagonist to the transporter is indicated as worth developing, and if a promising therapeutic application is uncovered by these animal model systems, activation or inhibition of the rB21a transporter is achieved therapeutically either by producing agonist or antagonist drugs directed against the mammalian rB21a transporter or by any method which increases or decreases the expression of the rB21a transporter in man.

Further provided by this invention is a method of determining the physiological effects of expressing varying levels of mammalian rB21a transporter which comprises producing a transgenic nonhuman animal whose levels of mammalian rB21a transporter expression are varied by use of an inducible promoter which regulates mammalian rB21a transporter expression. This invention also provides a method of determining the physiological effects of expressing varying levels of mammalian rB21a transporter which comprises producing a panel of transgenic nonhuman animals each expressing a different amount of mammalian rB21a transporter. Such animals may be produced by introducing different amounts of DNA encoding a mammalian rB21a transporter into the oocytes from which the transgenic animals are developed.

This invention also provides a method for identifying a substance capable of alleviating abnormalities resulting from overexpression of a mammalian rB21a transporter comprising administering the substance to a transgenic nonhuman mammal expressing at least one artificially introduced DNA molecule encoding a mammalian rB21a transporter and determining whether the substance alleviates the physical and behavioral abnormalities displayed by the transgenic nonhuman mammal as a result of overexpression of a mammalian rB21a transporter. As used herein, the term "substance" means a compound or composition which may be natural, synthetic, or a product derived from screening. Examples of DNA molecules are DNA or cDNA molecules having a coding sequence substantially the same as the coding sequences shown in FIG. 1.

This invention provides a pharmaceutical composition comprising an amount of the substance described supra effective to alleviate the abnormalities resulting from overexpression of a mammalian rB21a transporter and a pharmaceutically acceptable carrier.

This invention further provides a method for treating the abnormalities resulting from overexpression of a mammalian rB21a transporter which comprises administering to a subject an amount of the pharmaceutical composition described above effective to alleviate the abnormalities resulting from overexpression of a mammalian rB21a transporter.

This invention provides a method for identifying a substance capable of alleviating the abnormalities resulting from underexpression of a mammalian rB21a transporter comprising administering the substance to the transgenic nonhuman mammal described above which expresses only nonfunctional mammalian rB21a transporter and determining whether the substance alleviates the physical and behavioral abnormalities displayed by the transgenic nonhuman mammal as a result of underexpression of a mammalian rB21a transporter.

This invention also provides a pharmaceutical composition comprising an amount of a substance effective to alleviate abnormalities resulting from underexpression of rB21a transporter and a pharmaceutically acceptable carrier.

This invention further provides a method for treating the abnormalities resulting from underexpression of a mammalian rB21a transporter which comprises administering to a subject an amount of the pharmaceutical composition described above effective to alleviate the abnormalities resulting from underexpression of a mammalian rB21a transporter.

This invention provides a method of preparing the isolated rB21a transporter which comprises inducing cells to express rB21a transporter, recovering the transporter from the resulting cells, and purifying the transporter so recovered. An example of an isolated rB21a transporter is an isolated protein having substantially the same amino acid sequence as the amino acid sequence shown in FIG. 1. For example, cells can be induced to express transporters by exposure to substances such as hormones. The cells can then be homogenized and the transporter isolated from the homogenate using an affinity column comprising antibodies known to bind to the transporter. The resulting fractions can then be purified by contacting them with an ion exchange column, and determining which fraction binds anti-transporter antibodies.

This invention provides a method of preparing the isolated rB21a transporter which comprises inserting nucleic acid molecules encoding rB21a transporter in a suitable vector, inserting the resulting vector in a suitable host cell, recovering the rB21a transporter produced by the resulting cell, and purifying the rB21a transporter so recovered. An example of an isolated rB21a transporter is an isolated protein having substantially the same amino acid sequence as the amino acid sequence shown in FIG. 1. These methods for preparing rB21a transporter are well known in the art. For example, isolated nucleic acid encoding mammalian rB21a transporter is inserted in a suitable vector, such as an expression vector. A suitable host cell, such as a bacterial cell, or a eukaryotic cell such as a yeast cell, or an insect cell is transfected with the vector. Mammalian rB21a transporter is isolated from the culture medium by affinity purification or by chromatography or by other methods well known in the art.

This invention provides a method for determining whether a substrate not known to be capable of binding to a mammalian rB21a transporter can bind to a mammalian rB21a transporter which comprises contacting a mammalian cell comprising a DNA molecule encoding a mammalian rB21a transporter with the substrate under conditions permitting binding of substrates known to bind to transporters, detecting the presence of any of the substrate bound to the mammalian rB21a transporter, and thereby determining whether the substrate binds to the mammalian rB21a transporter. The DNA in the cell may have a coding sequence substantially the same as the coding sequences shown in FIG. 1, preferably, the mammalian cell is nonneuronal in origin. An example of a nonneuronal mammalian cell is a Cos7 cell. The preferred method for determining whether a substrate is capable of binding to the mammalian transporter comprises contacting a transfected nonneuronal mammalian cell (i.e. a cell that does not naturally express any type of transporter, thus will only express such a transporter if it is transfected into the cell) expressing a transporter on its surface, or contacting a membrane preparation derived from such a transfected cell, with the substrate under conditions which are known to prevail, and thus to be associated with, in vivo binding of the substrates to a transporter, detecting the presence of any of the substrate being tested bound to the transporter on the surface of the cell, and thereby determining whether the substrate binds to the transporter. This response system is obtained by transfection of isolated DNA into a suitable host cell. Such a host system might be isolated from pre-existing cell lines, or can be generated by inserting appropriate components into existing cell lines. Such a transfection system provides a complete response system for investigation or assay of the functional activity of mammalian rB21a transporter with substrates as described above. Transfection systems are useful as living cell cultures for competitive binding assays between known or candidate drugs and substrates which bind to transporters and which are labeled by radioactive, spectroscopic or other reagents. Membrane preparations containing the mammalian rB21a transporter isolated from transfected cells are also useful for these competitive binding assays. A transfection system constitutes a "drug discovery system" useful for the identification of natural or synthetic compounds with potential for drug development that can be further modified or used directly as therapeutic compounds to activate or inhibit the natural functions of the mammalian rB21a transporter. The transfection system is also useful for determining the affinity and efficacy of known drugs at the mammalian rB21a transporter sites.

This invention also provides a method of screening drugs to identify drugs which specifically interact with, and bind to, the mammalian rB21a transporter on the surface of a cell which comprises contacting a mammalian cell comprising a DNA molecule encoding a mammalian rB21a transporter on the surface of a cell with a plurality of drugs, determining those drugs which bind to the mammalian cell, and thereby identifying drugs which specifically interact with, and bind to, the mammalian rB21a transporter. Various methods of detection may be employed. The drugs may be "labeled" by association with a detectable marker substance (e.g., radiolabel or a non-isotopic label such as biotin). The DNA in the cell may have a coding sequence substantially the same as the coding sequences shown in FIG. 1. Preferably, the mammalian cell is nonneuronal in origin. An example of a nonneuronal mammalian cell is a Cos7 cell. Drug candidates are identified by choosing chemical compounds which bind with high affinity to the expressed rB21a transporter protein in transfected cells, using radioligand binding methods well known in the art, examples of which are shown in the binding assays described herein. Drug candidates are also screened for selectivity by identifying compounds which bind with high affinity to one particular transporter subtype but do not bind with high affinity to any other transporter subtype or to any other known transporter site. Because selective, high affinity compounds interact primarily with the target transporter site after administration to the patient, the chances of producing a drug with unwanted side effects are minimized by this approach. This invention provides a pharmaceutical composition comprising a drug identified by the method described above and a pharmaceutically acceptable carrier. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. Once the candidate drug has been shown to be adequately bioavailable following a particular route of administration, for example orally or by injection (adequate therapeutic concentrations must be maintained at the site of action for an adequate period to gain the desired therapeutic benefit), and has been shown to be non-toxic and therapeutically effective in appropriate disease models, the drug may be administered to patients by that route of administration determined to make the drug bioavailable, in an appropriate solid or solution formulation, to gain the desired therapeutic benefit.

This invention also provides a method of detecting expression of a rB21a transporter by detecting the presence of mRNA coding for a rB21a transporter. This method comprises obtaining total mRNA from the cell using methods well known in the art and contacting the mRNA so obtained with a nucleic acid probe as described hereinabove, under hybridizing conditions, detecting the presence of mRNA hybridized to the probe, and thereby detecting the expression of the transporter by the cell. Hybridization of probes to target nucleic acid molecules such as mRNA molecules employs techniques well known in the art. However, in one embodiment of this invention, nucleic acids are extracted by precipitation from lysed cells and the mRNA is isolated from the extract using a column which binds the poly-A tails of the mRNA molecules (Maniatis, T. et al., Molecular Cloning; Cold Spring Harbor Laboratory, pp. 197–98 (1982)). The mRNA is then exposed to radioactively labelled probe on a nitrocellulose membrane, and the probe hybridizes to and thereby labels complementary mRNA sequences. Binding may be detected by autoradiography or scintillation counting. However, other methods for performing these steps are well known to those skilled in the art, and the discussion above is merely an example.

Applicants have identified a novel transporter and have described methods for the identification of pharmacological compounds for therapeutic treatments. Pharmacological compounds which are directed against a specific transporter provide effective new therapies with minimal side effects.

Elucidation of the molecular structure of the neural rB21a transporter is an important step in the understanding of new neurotransmitters. This disclosure reports the isolation, amino acid sequence, mRNA localization, and functional expression of a cDNA clone from rat brain which encodes a rB21a transporter. Analysis of the mammalian rB21a transporter structure and function provides a possible model for the development of drugs useful for the treatment of migraine headaches, and brain swelling after injury, hypoxia, seizures, and stroke.

Specifically, this invention relates to the first isolation of a cDNA clone encoding a mammalian rB21a transporter. The new mammalian gene for this transporter has been characterized. The mRNA encoding rB21a exhibits a distinct regional and cellular pattern of distribution similar to that observed for other neurotransmitter transporters. In addition, the mammalian rB21a transporter has been expressed in Cos7 cells by transfecting the cells with the plasmid pcEXV-rB21a. The pharmacological binding properties of the protein encoded has been determined, and these binding properties classify this protein as a novel transporter.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

EXPERIMENTAL PROCEDURES

Cloning and Sequencing

A rat brain cDNA library in the Lambda ZAP II vector (Stratagene, La Jolla, Calif.) was screened at low stringency using probes representing the coding region of the rat GABA transporter (GAT-1) cDNA (Guastella et al., 1990). The probes were generated by polymerase chain reaction (PCR) amplification of randomly-primed rat brain cDNA using three sets of exact GAT-1 primers. The three sets of primers were designed such that the resulting PCR products represented the entire coding region as previously described (Smith et al., 1992). One of the PCR products was gel purified, subcloned, and sequenced to confirm its identity; the others were gel purified and used directly as probes. All three probes were labeled with $^{32}$P by the method of random priming (Feinberg and Vogelstein, 1983). Hybridization was performed at 40° C. in a solution containing 25% formamide, 10% dextran sulfate, 5×SSC (1×SSC is 0.15 M sodium chloride, 0.015 M sodium citrate), 1×Denhardt's (0.02% polyvinylpyrrolidone, 0.02% Ficoll, and 0.02% bovine serum albumin), and 100 µg/ml of sonicated salmon sperm DNA. The filters were washed at 40° C. in 0.1×SSC containing 0.1% sodium dodecyl sulfate (SDS) and exposed at −70° C. to Kodak XAR film in the presence of one intensifying screen. Lambda phage hybridizing to the probe were plaque purified and screened with the same probe mixture at high stringency to eliminate exact matches. rB21a clones were converted to phagemids by in vivo excision with f1 helper phage. Nucleotide sequences of double-stranded cDNAs in pBluescript were analyzed by the Sanger dideoxy nucleotide chain-termination method (Sanger, 1977) using Sequenase (U.S. Biochemical Corp., Cleveland, Ohio).

Expression

Two cDNA clones were identified which collectively span the entire coding region of the rB21a transporter gene, including 274 base pairs of 5' untranslated sequence and 902 base pairs of 3' untranslated sequence. The two clones were ligated at their internal BamHI sites to create a full-length 3.0 kb cDNA and subcloned into the eukaryotic expression vector pcEXV-3 (Miller and Germain, 1986) for pharmacological characterization.

Transient transfection of COS cells with rB21a was carried out using DEAE-dextran with DMSO according to the method of Lopata et al. (1984) with minor modifications. COS cells were grown in six-well plates (37° C., 5% $CO_2$) in high glucose Dulbecco's modified Eagle medium supplemented with 10% bovine calf serum, 100 U/ml penicillin G, and 100 µg/ml streptomycin sulfate. Cells were routinely used two days after transfection for transport studies.

Transport Studies

To measure transport of putative substrates, COS cells grown in 6-well plates (well diameter=35 mm) were washed 3×with HEPES-buffered saline (HBS, in mM: NaCl, 150; HEPES, 20; $CaCl_2$, 1; glucose, 10; KCl, 5; $MgCl_2$, 1; pH 7.4) and allowed to equilibrate in a 37° C. water bath. After 10 minutes the medium was removed and a solution containing 50 nM [$^3$H] substrate (6-90 Ci/mmole; New England Nuclear, Boston, Mass.) in HBS was added (1.5 ml/well). Plates were incubated at 37° C. for 10 or 20 minutes, then washed rapidly 3× with HBS. Cells were solubilized with 0.05% sodium deoxycholate/0.1 N NaOH (1 ml/well), 0.5 ml aliquots were removed, neutralized with 1N HCl, and radioactivity was determined by scintillation counting. Protein was quantified in an aliquot of the solubilized cells with the Bradford Reagent (Biorad, Richmond, Calif.), according to the manufacturer's directions. Non-specific uptake was defined in parallel wells with 1 mM unlabeled substrate.

Preparation of Cell Cultures

Primary cultures of neurons, Type 1 and 2 astrocytes, and meningeal and skin fibroblasts were prepared from E19 embryonic rats. Briefly, the brains were removed, dissected free of meninges, and trypsinized. Cells were dissociated mechanically by passage through a Pasteur pipet, and resuspended in DMEM containing 10% fetal bovine serum and antibiotics. The cells were added to tissue culture dishes that had been previously coated with 10 µM poly-D-lysine.

| | |
|---|---|
| Sense, 7/8 loop: CTGGAGGAGGTGAAGGACTACCTGGCATCTACTTACCCAAACAAG; | 5'- |
| Antisense, 7/8 loop: CTTGTTTGGGTAAGTAGATGCCAGGTAGTCCTTCACCTCCTCCAG; | 5'- |
| Sense, 3' UT: GTCACCTTTCTCTGAATCTAAGGTTCCTCACAGTGGGCCAGGACA; | 5'- |
| Antisense, 3' UT: TGTCCTGGCCCACTGTGAGGAACCTTAGATTCAGAGAAAGGTGAC. | 5'- |

Detailed methods for preparation of Type 1 and O-2A/Type 2 astrocyte cultures will be described in a subsequent communication (Borden et al., manuscript in preparation). For neurons, a plating density of 15×10$^6$ cells per 100 mm dish was employed; the medium was supplemented with insulin. Cytosine arabinoside (araC) was added to a final concentration of 10 µM on day 2 or 3 to inhibit the proliferation of non-neuronal cells. The neurons were harvested 1 week after plating. To obtain meningeal fibroblasts the meninges were trypsinized, then mechanically dissociated as described above. The cells recovered from a single embryo were plated into a 100 mm dish, grown to confluence, and passaged 1–2 times prior to harvesting. Fibroblasts from skin were prepared as described for meningeal cells.

Northern Blot Analysis of rB21a Transporter mRNA

Total cellular RNA was isolated from rat tissues and cells using guanidine isothiocyanate and collected by centrifugation through cesium chloride (MacDonald et al., 1987), as modified from the method of Chirgwin et al. (1979). Poly A+ RNAs were purchased from Clontech (Palo Alto, Calif.) or purified from total cellular RNA using the FastTrack kit (Invitrogen, San Diego, Calif.). Denatured RNA samples (5–25 µg) were separated in 1.0% agarose gels containing 2.7% formaldehyde. RNAs were transferred to GeneScreen Plus membranes (Dupont-NEN, Boston, Mass.) by overnight capillary blotting in 10×SSC. Northern blots were rinsed and then baked for 2 hours at 80° C. under vacuum. Prehybridization was for 1–2 hours at 42° C. in a solution containing 50% formamide, 1M sodium chloride, 10% dextran sulfate and 1.0% SDS. Blots were hybridized overnight at 42° C. with 32P-labeled rB21a cDNA (randomly primed) in prehybridization mixture containing 100 µg/ml sonicated salmon sperm DNA. The blots were washed successively in 2×SSC/2% SDS, 1×SSC/2% SDS, and 0.2×SSC/2% SDS at 65° C., then exposed to Kodak XAR-5 film with one intensifying screen at −80° C. for up to one week. After hybridization with rB21a, blots were routinely reprobed with 1B15 (Danielson et al., 1988) in order to confirm that equal amounts of RNA were present in each lane.

In Situ Hybridization

Male Sprague-Dawley rats (150–250 g) were decapitated and their brains and peripheral tissues were rapidly removed and frozen in isopentane on dry ice. Tissues were sectioned on a cryostat, thaw-mounted onto poly-L-lysine-coated slides, and stored at −20° C. until use. Pairs of antisense and sense oligonucleotides designed to the 7/8 loop and the 3'-untranslated region were synthesized on a Cyclone Plus DNA Synthesizer (Milligen/Bioresearch). The sequences of the oligonucleotides (45 mers) were:

Probes were 3'-end labeled with 35S-dATP (1200 Ci/mmol, New England Nuclear, Boston, Mass.) to a specific activity of 10$^9$ dpm/µg using terminal deoxynucleotidyl transferase (Boehringer Mannheim, Indianapolis, Ind.). Hybridization buffer consisted of 50% formamide, 4×SSC (1×SSC=0.15M NaCl and 0.015M sodium citrate), 1×Denhardt's solution (0.2% polyvinyl-pyrrolodine, 0.2% Ficoll, 0.2% bovine serum albumin), 50 mM dithiothreitol, 0.5 mg/ml yeast tRNA, and 10% dextran sulfate. Radiolabeled probe in 100 µl hybridization buffer was applied to each tissue section and hybridized overnight at 50° C. Sections were washed for 2×30 minutes in 2×SSC at room temperature, for 1 hour in 1×SSC at room temperature, for 1 hour in 2×SSC at 50° C., and for 30 minutes in 0.1×SSC at room temperature. Tissues were dehydrated in a series of graded alcohols, apposed to Kodak XAR-5 film for two weeks, then dipped in Kodak NTB3 autoradiography emulsion diluted 1:1 with 0.2% glycerol. After four weeks, slides were developed and counterstained with hematoxylin and eosin, and the cellular distribution of the exposed silver grains was examined with a Zeiss Axioskop. Parallel tissues pretreated with 100 µg/ml RNase A (37° C., 30 minutes) prior to hybridization showed no significant signal. Both pairs of oligonucleotides for rB21a (see above) showed identical patterns of hybridization.

RESULTS

Cloning

In order to clone novel neurotransmitter transporters we screened a rat brain cDNA library at low stringency with probes encoding the rat GABA transporter GAT-1 (Guastella et al., 1990). Using this approach we succeeded in cloning the glycine transporter (Smith et al., 1992), the taurine transporter (Smith et al., 1992a), and two novel GABA transporters (Borden et al., 1992). An additional clone was identified that hybridized at low but not at high stringency with the GABA transporter probes, indicating it was related but not identical to GAT-1. DNA sequence analysis revealed that the clone encoded a putative transporter with 53% nucleotide identity to GAT-1. The full-length cDNA, rB21a, contained a 3.0 kb sequence with an open reading frame of 1848 base pairs which could encode a protein of 616 amino acids.

Searches of GenBank and EMBL data bases demonstrated that the nucleotide sequence of rB21a was novel and that the most closely related sequences (46–53%) were those encoding neurotransmitter transporters such as GAT-1 (Guastella et al., 1990), BGT-1 (Yamauchi et al., 1992), the dopamine transporter (Shimada et al., 1991), and the norepinephrine transporter (Pacholczyk et al., 1991). A recent search indicates that rB21a exhibits slightly higher nucleotide identity (~56%) to an unidentified transporter designated NTT4 (Liu et al., 1993a).

Amino acid sequence deduced from the nucleotide sequence of the rB21a cDNA is shown in FIG. 1 and includes a methionine for translation initiation and a stop codon. The translation product of rB21a is predicted to have a relative molecular mass of ~67,000 Daltons; hydropathy analyses indicate the presence of 12 hydrophobic regions which may represent transmembrane domains (TMs). One potential site for Asn-linked glycosylation is found in the extracellular loop between the third and fourth TMs, a feature shared with previously cloned members of this gene family which have at least one site in this region. The novel transporter also has a potential glycosylation site in the predicted extracellular loop between TMs seven and eight, a feature that distinguishes it from previously cloned neurotransmitter transporters. Interestingly, alignment of the deduced amino acid sequence of rB21a with those of the GAT-2, taurine, glycine, and norepinephrine transporters (FIG. 2) reveals that despite regions of high sequence conservation, the novel transporter is predicted to have a significantly longer ⅞ loop. Together with two unidentified transporters recently cloned from rat brain (Uhl et al., 1992; Liu et al., 1993a), which are also predicted to have large extracellular loops between TMs seven and eight, rB21a may represent a structural subfamily within the transmitter transporter gene family.

A summary of the overall amino acid sequence comparisons among transporters is shown in Table 1. In agreement with nucleotide sequence comparisons, the novel transporter rB21a is most closely related to a variety of neurotransmitter transporters (36–41%), but not as closely related as subtypes known to transport the same substrate, such as GAT-2 and GAT-3 (67%). Rather, the amino acid identity of rB21a with the other transporters is similar to transporters within the same family that transport different substrates (ie., glycine vs. taurine, ~41%). Much lower amino acid identity (~18%) is seen with unrelated transporters such as the sodium/glucose cotransporter (Hediger et al., 1989).

TABLE 1

Amino Acid Identities of rB21a
with the Neurotransmitter Transporter Family
AMINO ACID IDENTITY (Percent)

| Transporter | rB21a |
| --- | --- |
| GABA (GAT-1) | 38.3 |
| GABA (GAT-2) | 39.8 |
| GABA (GAT-3) | 38.6 |
| Taurine | 39.5 |
| Betaine/GABA (BGT-1) | 40.5 |
| Glycine | 40.1 |
| L-Proline | 36.8 |
| Norepi | 36.7 |
| Dopamine | 36.1 |
| Serotonin | 36.4 |
| Creatine | 40.3 |
| sodium/glucose | 17.3 |

Pharmacology

These sequence comparisons suggested that rB21a might encode an additional neurotransmitter transporter expressed in the brain. To explore this possibility, a cDNA containing the full coding region of the rB21a transporter was placed in a mammalian expression vector (pcEXV-3), transfected into COS cells, and screened for transport of a variety of radiolabeled neurotransmitters and amino acids. COS cells transiently transfected with rB21a (COS/rB21a) failed to accumulate a variety of tritiated substrates to a greater extent than non-transfected control cells (see Table 2). The substrates tested included the inhibitory amino acid neurotransmitters, the monoamine neurotransmitters, and several amino acids and other related endogenous compounds. It is possible that rB21a does encode a transporter for one of the substrates tested, but that some aspect of the test system prevented expression of the transporter protein at sufficient levels for detection. Alternatively, the cDNA may contain an artifact which prevents correct expression of the protein. Specific antibodies will be necessary to assess expression at the cell surface; however, we have successfully expressed many related transporters in the same model systems. Thus, despite significant sequence homology with the family of neurotransmitter transporters, the rB21a cDNA does not appear to encode a transporter for commonly known classical neurotransmitters.

TABLE 2

Potential Substrates Tested for Transport at rB21a

Adenosine
Choline
Histamine
Glutamate
Tyrosine
GABA
Dopamine
Norepinephrine
Lysine
Serotonin
Taurine
Glycine
Melatonin
Alanine (for system ASC)
α-(Methylamino) isobutyric acid (for system A)

Cos-7 cells transfected with rB21a were incubated for 10 minutes at 37° C. with 50 nM $^3$H-substrate. Non-specific uptake was defined in the presence of 1 mM unlabeled substrate. rB21a showed no specific uptake for the compounds listed.

Localization

In order to gain insight into the potential function of the rB21a transporter, we carried out localization studies of the mRNA encoding the transporter. Northern blot analysis of polyA+ RNAs from various rat tissues revealed a 3 kb transcript in brain, kidney, and lung that hybridized at high stringency with rB21a (FIG. 3). In the kidney, an additional ~2.6 kb hybridizing transcript was present which could represent either a related mRNA (transporter subtype) expressed only in kidney, or tissue-specific expression of an alternatively spliced transcript of rB21a; we cannot currently distinguish between these possibilities. Quantitation of the rB21a mRNA relative to 1B15 (data not shown) confirmed that the highest levels of rB21a mRNA were present in the brain, with lower levels in kidney and lung. Low amounts of retina and pancreas RNA on the blot preclude assessment of rB21a levels in those tissues. A pattern of distribution in which brain and selected peripheral tissues express transporter mRNA has been observed for the GABA transporter GAT-2 (Borden et al., 1992).

To explore the distribution of the novel transporter within the brain, Northern blot analysis of polyA+ RNA from various rat brain regions was carried out as described in Experimental Procedures. For rB21a, the level of the 3 kb transcript was most abundant in cerebellum, followed by the olfactory bulb, after an overnight exposure of the autoradiogram (FIG. 4). rB21a transcripts within the brain therefore reveal a distinct pattern of distribution with respect to location and abundance.

To complement and extend the Northern analyses of rB21a mRNA, in situ hybridization studies were carried out in sections of rat brain and kidney. As shown in FIG. 5, the mRNA encoding rB21a is abundant in the leptomeninges (pia) but not elsewhere in the brain. In the kidney, in agreement with Northern blot analysis, the transcript is less abundant; its pattern of distribution is limited to the outer medullary layer, which contains proximal convoluted tubules as well as ascending and descending limbs of the loop of Henle.

Figure 6:
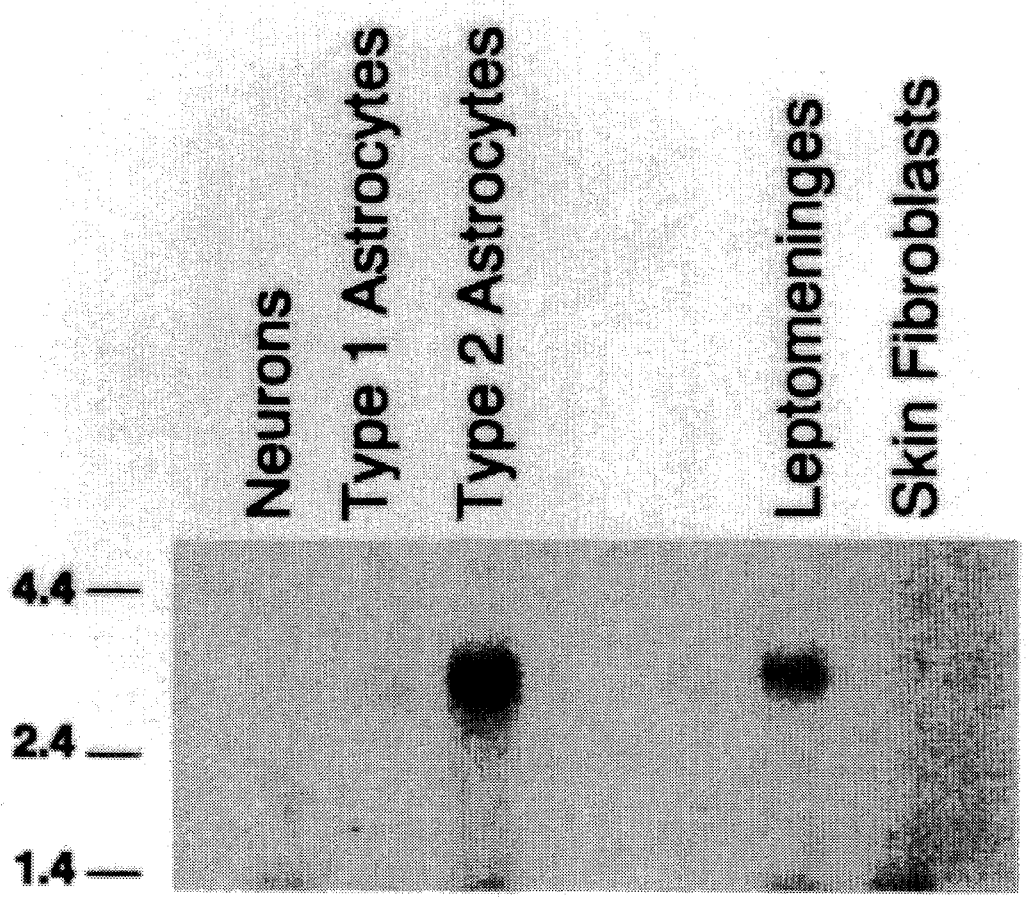
FIG. 6. Northern Blot Analysis of rB21a in Rat Brain Cultures. Northern blots of total RNA isolated from cultured neurons, astrocytes, meningeal cells, and skin fibroblasts (25 µg) were prepared as described for FIG. 3. A ~3 kb hybridizing transcript is present in Type 2 astrocytes and meningeal cells (5 day exposure).

To ascertain which cell types in the brain express each transporter, we examined the cellular distribution of rB21a mRNA by Northern blot analysis of total RNA isolated from cultured neurons, Type 1 and 2 astrocytes, leptomeningeal cells, and skin fibroblasts (FIG. 6). Interestingly, rB21a was predominantly expressed in Type 2 astrocytes and leptomeningeal cells, with no detectable signal in neurons or skin fibroblasts; a very faint signal can be seen in Type 1 astrocytes. The distinct regional and cellular patterns of distribution of rB21a are suggestive of a specialized function for the transporter, in contrast with a generalized distribution expected of a ubiquitous metabolite transporter.

DISCUSSION

We have cloned a novel rat brain cDNA, designated rB21a, that encodes a protein with significant homology to the recently described family of sodium-dependent neurotransmitter transporters. The mRNA is present in the brain, and exhibits a distinct pattern of regional and cellular distribution. Its endogenous substrate has not yet been identified; however, its sequence conservation and restricted localization within the nervous system suggests functional as well as structural homology with the neurotransmitter transporters.

Sequence homology is not sufficient to define the physiological role of a protein, but members of this gene family have many functional similarities which may extend to "orphan" transporters. Of the eleven transporters whose substrates have been characterized (see Introduction), all are expressed in the brain and all but one (creatine transporter; Guimbal and Kilimann, 1993) have substrates believed to be neurotransmitters or neuromodulators, though they may have other functions outside the brain.

Neurotransmitter transporters typically exhibit a high degree of selectivity for a specific substrate, but in some cases can transport multiple substrates; for example, the BGT-1 (betaine/GABA) transporter is believed to transport GABA (an inhibitory neurotransmitter) in the brain and betaine (an osmoregulator) in the kidney (Yamauchi et al., 1992; Lopez-Corcuera et al., 1992). Similarly, the transporter for taurine, an osmoregulator present in brain and peripheral tissues, also transports the putative amino acid neurotransmitter β-alanine with high affinity (Uchida et al., 1992; Smith et al., 1992a; Liu et al., 1992). This demonstrates that a single transporter protein can subserve multiple functions, and that the identification of one transported substrate does not necessarily define all the functions of the transporter. Further, the existence of multiple transporter subtypes for a single substrate such as GABA (GAT-1, GAT-2, GAT-3, and BGT-1; Guastella et al., 1990; Borden et al., 1992; Yamauchi et al., 1992) complicates the determination of function even when the substrate is known. Thus, for the orphan transporter rB21a, the identification of a high-affinity substrate will be helpful but not definitive in elucidating the therapeutic applications of this gene product.

When structure/function relationships within the neurotransmitter transporter gene family are better understood, it may be possible to predict interactions with substrates and inhibitors based on amino acid sequence alone. The cloning of the cDNA encoding rB21a has nevertheless provided the means to explore its physiological roles by pharmacological characterization, and by Northern and in situ mapping of its mRNA distribution. Further, the availability of the cDNA encoding the transporter facilitates the development of specific antibodies and antisense technologies useful in defining the functions of the gene product in vivo. Antisense oligonucleotides which target mRNA molecules to selectively block translation of the gene product in vivo have been used successfully to relate the expression of a single gene with its functional sequelae. For example, treatment of rats with antisense oligonucleotides directed against the neuropeptide Y1 receptor resulted in decreased Y1 receptor binding and production of an anxiety-like state in the rats (Wahlestedt et al., 1993). Similarly, the role of NMDA receptors in neurotoxicity after ischemia has been successfully probed (Wahlestedt et al., 1993a). The cloning of rB21a allows the use of this approach to explore the functional consequences of blocking the expression of its mRNA without knowledge of its substrate.

Therapeutic agents acting at transporters can potentially affect a wide variety of physiological processes. In the brain, neurotransmitter transporters serve to terminate synaptic transmission by the rapid removal of transmitter from the synapse, and recycle neurotransmitter for rerelease or other metabolic needs; they may also release transmitter via reversal of transporter, or regulate levels of non-synapticly released mediators to modulate neurotransmission. Transporters in peripheral tissues such as kidney and lungs metabolize neurotransmitters and control the concentration of a variety of organic solutes; in the kidney, transporters are responsible for the reabsorption of electrolytes, amino acids, and other nutrients prior to the excretion of waste. Transporters can also serve as binding sites for exogenous substances and organisms; for example, the basic amino acid transporter y+ is also a viral permease (Wang et al., 1991; Kim et al., 1991). Drugs interacting at these sites to either block or facilitate transport could affect all of the functions described above.

Our localization studies have provided clues as to the potential clinical applications of rB21a. The presence of rB21a in the lung, kidney, and leptomeninges (pia) of the brain suggests a role in fluid balance. Transporters in the pia could regulate the composition and volume of cerebrospinal fluid (CSF) and brain extracellular fluid, and thereby play an important role in states such as migraine, and in homeostatic mechanisms to control brain swelling after injury, hypoxia, seizures, or stroke. Pial transporters are situated to control the concentration of solutes such as neurotransmitters in the CSF; changes in levels of CSF neurotransmitters or metabolites can have profound effects on brainstem centers controlling functions such as respiration and blood pressure.

In summary, we provide evidence that the novel transporter encoded by the rB21a cDNA is a member of the neurotransmitter transporter gene family based on sequence homology and localization studies. The cloning of this gene provides the means to elucidate its physiological role in the nervous system and to develop novel therapeutic agents acting at this target.

What is claimed is:

1. An isolated nucleic acid molecule encoding a rat rB21a transporter having the amino acid sequence shown in SEQ. I.D. No. 2.

2. An isolated nucleic acid molecule of claim 1, wherein the nucleic acid molecule is a DNA molecule.

3. An isolated DNA molecule of claim 2, wherein the DNA molecule is a cDNA molecule.

4. A vector comprising the nucleic acid molecule of claim 1.

5. A plasmid comprising the vector of claim 4.

6. A vector of claim 4 which further comprises bacterial regulatory elements operably linked to the nucleic acid molecule encoding the rat rB21a transporter.

7. A vector of claim 4 which further comprises yeast regulatory elements operably linked to the nucleic acid molecule encoding the rat rB21a transporter.

8. A vector of claim 4 which further comprises insect regulatory elements operably linked to the nucleic acid molecule encoding the rat rB21a transporter.

9. A vector of claim 4 which further comprises mammalian regulatory elements operably linked to the nucleic acid molecule encoding the rat rB21a transporter.

10. A plasmid comprising the cDNA molecule of claim 3 designated pcEXV-rB21a (ATCC Accession No. 75609).

11. A mammalian cell comprising the plasmid encoding the rB21a transporter of claim 10.

12. The mammalian cell of claim 11, wherein the cell is a Cos7 cell.

13. An insect cell comprising the vector of claim 8.

14. A bacterial cell comprising the vector of claim 6.

15. A yeast cell comprising the vector of claim 7.

\* \* \* \* \*